United States Patent [19]
Uzan et al.

[11] Patent Number: 6,103,705
[45] Date of Patent: Aug. 15, 2000

[54] PHARMACEUTICAL COMPOSITION COMPRISING A COMPOUND HAVING ANTI-XA ACTIVITY AND A PLATELET AGGREGATION ANTAGONIST COMPOUND

[75] Inventors: Andre Uzan, Paris, France; Alain H. Curaudeau, Devon; Robert J. Leadley, Collegeville, both of Pa.; Christopher T. Dunwiddie, Carmel, Ind.; Mark H. Perrone, Chalfont, Pa.

[73] Assignee: Aventis Pharmaceuticals Products Inc., Collegeville, Pa.

[21] Appl. No.: 09/192,710

[22] Filed: Nov. 16, 1998

Related U.S. Application Data

[63] Continuation of application No. PCT/US97/21440, Nov. 24, 1997, which is a continuation-in-part of application No. 60/031,878, Nov. 27, 1996, abandoned.

[51] Int. Cl.[7] ...................... A61K 31/725; A61K 31/445
[52] U.S. Cl. .............................................. 514/56; 514/331
[58] Field of Search ....................... 514/56, 331

[56] References Cited

U.S. PATENT DOCUMENTS

| | | |
|---|---|---|
| 3,766,167 | 10/1973 | Lasker et al. . |
| 4,438,108 | 3/1984 | Sanders et al. . |
| 4,486,420 | 12/1984 | Lormeau et al. . |
| 4,533,549 | 8/1985 | Lasker . |
| 4,629,699 | 12/1986 | Bianchini . |
| 4,683,291 | 7/1987 | Zimmerman et al. . |
| 4,692,435 | 9/1987 | Lormeau et al. . |
| 4,804,652 | 2/1989 | Lormeau et al. . |
| 4,826,827 | 5/1989 | Lormeau et al. . |
| 4,857,508 | 8/1989 | Adams et al. . |
| 4,879,313 | 11/1989 | Tjoeng et al. . |
| 4,952,562 | 8/1990 | Klein et al. . |
| 4,992,463 | 2/1991 | Tjoeng et al. . |
| 5,023,233 | 6/1991 | Nutt et al. . |
| 5,037,808 | 8/1991 | Tjoeng et al. . |
| 5,051,405 | 9/1991 | Klein et al. . |
| 5,053,392 | 10/1991 | Klein et al. . |
| 5,064,814 | 11/1991 | Klein et al. . |
| 5,086,069 | 2/1992 | Klein et al. . |
| 5,100,875 | 3/1992 | Marguerie de Rotrou . |
| 5,292,756 | 3/1994 | Duggan et al. . |
| 5,639,469 | 6/1997 | Benes et al. . |
| 5,721,214 | 2/1998 | Marlowe et al. ............ 514/18 |
| 5,763,427 | 6/1998 | Wertz et al. ............... 514/56 |

FOREIGN PATENT DOCUMENTS

| | | |
|---|---|---|
| 040 144 | 11/1981 | European Pat. Off. . |
| 066 908 | 12/1982 | European Pat. Off. . |
| 014 184 | 8/1984 | European Pat. Off. . |
| 076 279 | 9/1986 | European Pat. Off. . |
| 244 235 | 11/1987 | European Pat. Off. . |
| 244 236 | 11/1987 | European Pat. Off. . |
| 269 981 | 6/1988 | European Pat. Off. . |
| 319 506 | 7/1989 | European Pat. Off. . |
| 347 588 | 12/1989 | European Pat. Off. . |
| 380 943 | 8/1990 | European Pat. Off. . |
| 478 362 | 4/1992 | European Pat. Off. . |
| 479 481 | 4/1992 | European Pat. Off. . |
| 037 319 | 6/1995 | European Pat. Off. . |
| 81/03276 | 11/1981 | WIPO . |
| WO 89/11538 | 11/1989 | WIPO . |
| WO 91/04746 | 4/1991 | WIPO . |
| WO 92/13117 | 8/1992 | WIPO . |
| WO 92/19249 | 11/1992 | WIPO . |
| WO 93/08845 | 5/1993 | WIPO . |
| WO 95/10295 | 4/1995 | WIPO . |
| WO 95/34286 | 12/1995 | WIPO . |
| WO 97/35592 | 10/1997 | WIPO . |

OTHER PUBLICATIONS

Wenzl et al., Loss of Extremities in Heparin–Induced Thrombocytopenia, Unfallchirurg 99:607–611 (1996).

Genetta et al., Abciximab: A New Antiaggregant Used in Angioplasty, The Annals of Pharmacotherapy, (30) 251–257 (1996).

Riessen et al., Prospects for Site–Specific Delivery of Pharmacologic and Molecular Therapies, JACC 23(5), 1234–1244 (1994).

Topol et al., Randomised trial of coronary intervention with antibody against platelet 11b/111a integrin for reduction of clinical restenosis: results at six months, The Lancet 343, 881–886 (1994).

Cremonesi et al., Structural And Biological Aspects of Low–Molecular Weight Heparins, Drugs of the Future 12(1), 45–64 (1987).

Plow et al., Inhibition of fibrinogen binding to human platelets by the tetrapeptide glycyl–L–arginyl–L–proline, Proc. Natl. Acad. Sci., USA 79, 3711–3715 (1982).

Ruggeri et al., Inhibition of platelet function with synthetic peptides designed to be high–affinity antagonists of fibrinogen binding to platelets, Proc. Natl. Acad. Sci., USA 83, 5708–5712 (1986).

(List continued on next page.)

*Primary Examiner*—Zohreh Fay
*Attorney, Agent, or Firm*—Raymond S. Parker, III; Christine M. Hansen; Ross J. Oehler

[57] ABSTRACT

The invention is also directed to pharmaceutical composition comprising a compound having anti-Xa activity, a platelet aggregation antagonist compound and a pharmaceutically acceptable carrier. The invention is also directed to a method of treating or preventing a thrombogenic condition associated with a thrombosis related ischemic disorder in a patient comprising administering to said patient pharmaceutically effective amounts of a compound having anti-Xa activity and a platelet aggregation antagonist compound. In addition, this invention is directed to the use of pharmaceutically effective amounts of a compound having anti-Xa activity and a platelet aggregation antagonist compound in the preparation of a medicament for treating or preventing a physiological condition associated with thrombosis related ischemic disorder. Furthermore, this invention is directed to a kit for treating or preventing a physiological condition associated with thrombosis related ischemic disorder, said kit comprising a plurality of separate containers, wherein at least one of said containers contains a compound having anti-Xa activity and at least another of said containers contains a platelet aggregation antagonist compound, and said containers optionally contain a pharmaceutical carrier.

36 Claims, 12 Drawing Sheets

OTHER PUBLICATIONS

Plow et al., The effect of Arg–Gly–Asp–containing peptides on fibrinogen and von Willebrand factor binding to platelets, Proc. Natl. Acad. Sci. USA 82, 8057–8061 (1985).

Cook et al., The Effects of Two Synthetic Glycoprotein 11b/111a Antagonists, Ro 43–8857 and L–700,462, on Platelet Aggregation and Bleeding in Guinea–Pigs and Dogs: Evidence that Ro 43–8857 Is Orally Active, Thrombosis & Haemostasis 70(5), 883–847 (1993).

Kereiakes et al., Randomized, Double–Bline, Placebo–Controlled Dose–Ranging Study of Tirofiban (MK–383) Platelet 11b/111a Blockade in High Risk Patients Undergoing Coronary Angioplasty, JACC 27(3), 536–542 (1996).

Haverstick et al., Inhibition of Platelet Adhesion to Fibronectin, Fibrinogen, and von Willebrand Factor Substrates by a Synthetic Tetrapeptide Derived From the Cell–Binding Domain of Fibronectin, Blood 66(4), 946–952 (1985).

Barrett et al., Pharmacokinetics and pharmacodynamics of MK–383, a selective non–peptide platelet glycoprotein–11b/111a receptor antagonist, in healthy men, Clinical Pharmacology & Therapeutics 56(4), 377–388 (1994).

Ginsberg et al., Inhibition of Fibronectin Binding to Platelets by Proteolytic Fragments and Synthetic Peptides Which Support Fibroblast Adhesion*, Journal of Biological Chemistry 260(7), 3931–3936 (1985).

Gartner et al., The Tetrapeptide Analogue of the Cell Attachment Site of Fibronectin Inhibits Platelet Aggregation and Fibrinogen Binding to Activated Platelets*, Journal of Biological Chemistry 260(22), 11891–11894 (1985).

Dettori et al., Human Pharmacology of a Low–Molecular–Weight Heparin (Alfa–LMWH): An Update, Medicinal Research Reviews 12(4), 373–389 (1992).

Zammit et al., Low–Affinity Material Does Not Contribute to the Antithrombotic Activity of Organ (Org 10172) in Human Plasma, Thromb. Haemostas. 71(6), 759–767 (1994).

Lynch et al., Nonpeptide Glycoprotein 11b/111a Inhibitors 5. Antithrombotic Effects of MK–0383, Jnl of Pharmacology & Experimental Therapeutics 272(1), 2–32 (1995).

Barrowcliffe et al., Anticoagulant Activities of Lung & Mucous Heparins, Thrombosis Research 12, 27–36 (1977).

Gent et al., Low–Molecular–Weight Heparinoid Orgaran In More Effective Than Aspirin in the Prevention of Venous Thromboembolism After Surgery for Hip Fracture, Circulation 93(1) 80–84 (1996).

Catalfamo et al., Isolation of Platelets from Laboratory Animals, Methods in Enzymology 169, 117–133 (1989).

Peerlinck et al., MK–383 (L–700,462), a Selective Nonpeptide Platelet Glycoprotein iib/iiia Antagonist, Is Active in Man, Circulation 88(4), Part 1, 1512–1517 (1993).

Fussi, F. et al., Methods of Heparin depolymerization: oligoheteropolysaccharides as antithrombotic agents. New frontiers in prophylaxis of venous thrombosis., pp. 339–345.

Frederick, Leo G. et al., The Protective Dose of the Potent GPIIb/IIIa Antagonist SC–54701A Is Reduced When Used in Combination With Aspirin and Heparin in a Canine Model of Coronary Artery Thrombosis.

Green et al., Interaction of Low Molecular Weight Heparin With Ketorolac, J. Lab Clin. Med, pp. 583–587 (1996).

Leadley, Robt. J. Jr et al., Inhibition of Repetitive Thrombus Formation in the Stenosed Canine Coronary Artery by Enoxaparin, But Not by Unfractionated Heparin, Arterioscler. Thromb. Vasc. Biol., vol. 18, pp. 908–914 (1998).

Bernat, A. et al., The Antithrombotic Efficacy of the GP IIb/IIIa Antagonist SR121787 is Potentiated by Antithrombin–Dependent Factor Xa Inhibition Without an Increase in the Bleeding Risk in the Rabbit, Journal of Cardio. Pharm. vol. 33, No. 4, pp. 573–579 (1999).

New International Study of ReoPro in Acute Coronary Syndrome Underway; Substudy Will Assess Safety of Reopro(R) and Fragmin(R) in Combination, PR Newswire (4); Mar. 30, 1999.

Verheggen, P.W.H.M. et al., Inflammatory Status as a Main Determinant of Outcome in Patients with Unstable Angina, Independent of Coagulation Activation and Endothelial Cell Function, European Heart Journal, vol. 20, pp. 567–574 (1999).

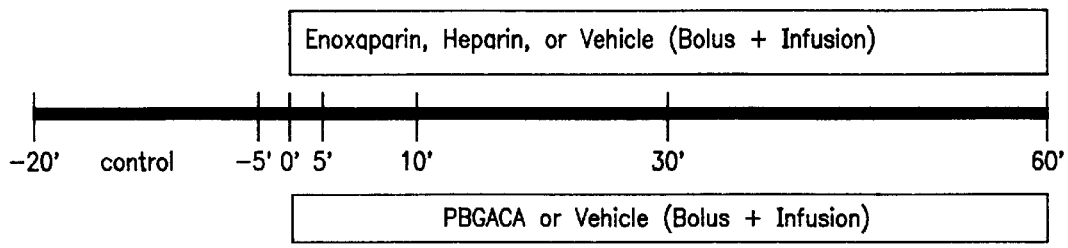

Blood Sampling/Hemodynamics

Arterial samples at -5, 5, 10, 30, 60 min
- APTT, PT
- Anti-Xa, Anti IIa
- Template Bleeding Time
- Platelet Count
- Platelet Aggregation (ADP, Collagen, Thrombin, AA)

- Coronary Blood Flow (CFRs per 20 min periods)

Treatment Groups (n=5 per group)

- PBGACA low (10 μg/kg+0.15 μg/kg/min)
- PBGACA high (30 μg/kg+0.45 μg/kg/min)
- Enoxaparin (0.5 mg/kg+5 μg/kg/min)
- Enoxaparin (0.5 mg/kg+5 μg/kg/min) plus PBGACA low
- Heparin (60 U/kg+0.7 U/kg/min)
- Heparin (60 U/kg+0.7 U/kg/min) plus PBGACA low

FIG. 13

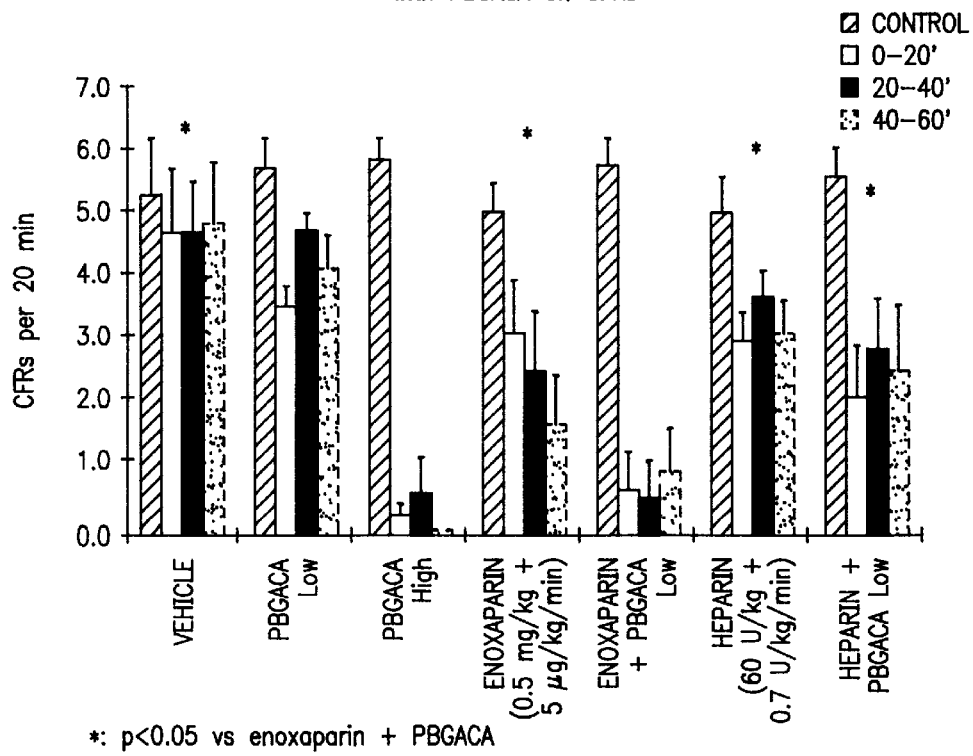

*: p<0.05 vs enoxaparin + PBGACA

FIG. 14

PHARMACEUTICAL COMPOSITION COMPRISING A COMPOUND HAVING ANTI-XA ACTIVITY AND A PLATELET AGGREGATION ANTAGONIST COMPOUND

This application is a continuation application of copending PCT US97/21440, filed Nov. 24, 1997, which designates the United States, which, in turn, is a continuation-in-part application of U.S. patent application Ser. No. 60/031,878, filed Nov. 27, 1996, now abandoned.

FIELD OF THE INVENTION

This invention is directed to a pharmaceutical composition comprising an anti-Xa activity compound and a platelet aggregation antagonist compound which exhibits unexpectedly efficacious activity for treating or preventing a physiological condition associated with a thrombosis related ischemic disorder in a patient. The invention is also directed to a method of treating or preventing a thrombogenic condition associated with a thrombosis related ischemic disorder in a patient comprising administering pharmaceutically effective amounts of an anti-Xa activity compound and a platelet aggregation antagonist compound.

Platelet fibrinogen receptor antagonists have been shown to be effective agents for inhibiting platelet-dependent thrombus formation in animal models of coronary thrombosis. Likewise, results from clinical studies have shown that platelet fibrinogen receptor antagonists reduce the composite incidence of major ischemic events when administered to high-risk patients undergoing percutaneous transluminal coronary angioplasty. However, the therapeutic window is very narrow for this class of compounds, in part, because the high degree of inhibition of ex vivo platelet aggregation required for antithrombotic efficacy is often associated with a marked increase in template bleeding time, which is a marker of an undesirable bleeding complications.

Low molecular weight heparins (LMWHs) and heparinoid compounds (HCs) have been used effectively over the past few years for the prevention and treatment of venous thrombosis and the associated thromboembolism. However, LMWHs and HCs are gradually pervading into the treatment repertoire for arterial thrombotic indications. Preliminary results favoring the use of LMWH or HCs over unfractionated heparin in arterial thrombotic indications are supported by several pharmacodynamic, pharmacokinetic, and mechanistic differences between these two classes of compounds. For example, reliable and safe anticoagulation can be achieved with LMWHs or HCs by subcutaneous dosing without monitoring. Compared to heparin, LMWHs and HCs have a higher bioavailability, a relatively long half-life, and appear to have a safer profile. In addition, LMWHs are more resistant than heparini to neutralization by platelet factor 4, which is released from activated platelets, presumably at the site of arterial thrombosis.

Haemostasis, the biochemistry of blood coagulation, is an extremely complex phenomena whereby normal whole blood and body tissue spontaneously arrest bleeding from injured blood vessels. Effective haemostasis requires the combined activity of vascular, platelet and plasma factors as well as a controlling mechanism to prevent excessive clotting. Defects, deficiencies, or excesses of any of these components can lead to hemorrhagic or thrombotic consequences.

Platelet adhesion, spreading and aggregation on extracellular matrices are central events in thrombus formation. These events are mediated by a family of adhesive glycoproteins, i.e., fibrinogen, fibronectin, and von Willebrand factor. Fibrinogen is a co-factor for platelet aggregation, while fibronectin supports platelet attachments and spreading reactions, and von Willebrand factor is important in platelet attachment to and spreading on subendothelial matrices. The binding sites for fibrinogen, fibronectin and von Willebrand factor have been located on the platelet membrane protein complex known as glycoprotein IIb/IIIa.

Adhesive glycoproteins, like fibrinogen, do not bind with normal resting platelets. However, when a platelet is activated with an agonist such as thrombin or adenosine diphosphate, the platelet changes its shape, perhaps making the GPIIb/IIIa binding site accessible to fibrinogen. Blocking the fibrinogen receptor, thus inhibits platelet aggregation and subsequent thrombus formation, and is useful for the prevention and treatment of pathological thrombogenic conditions, such as stroke, peripheral arterial occlusive disease, disseminated intravascular coagulation, and acute coronary syndromes such as unstable angina and myocardial infarction.

SUMMARY OF THE INVENTION

The invention is also directed to pharmaceutical composition comprising a compound having anti-Xa activity, a platelet aggregation antagonist compound and a pharmaceutically acceptable carrier. The invention is also directed to a method of treating or preventing a thrombogenic condition associated with a thrombosis related ischemic disorder in a patient comprising administering to said patient pharmaceutically effective amounts of a compound having anti-Xa activity and a platelet aggregation antagonist compound.

BRIEF DESCRIPTION OF THE FIGURES

FIG. 13 represents information regarding assorted blood sampling/hemodynamic measurements during administration of different concentrations of the anti-Xa activity compound, Enoxaparin, the platelet aggregation antagonist compound, N-[N-[N-(4-(piperidin-4-yl)butanoyl)-N-ethylglycyl]aspartyl]-L-β-cyclohexyl alanine amide (PBGACA), and composition thereof over time.

FIG. 14 represents a graph of the number of cyclic flow reductions (CFRs) for different concentrations of the anti-Xa activity compound, Enoxaparin, the platelet aggregation antagonist compound, PBGACA, and composition thereof over time.

DETAILED DESCRIPTION OF THE INVENTION

Figure 1:
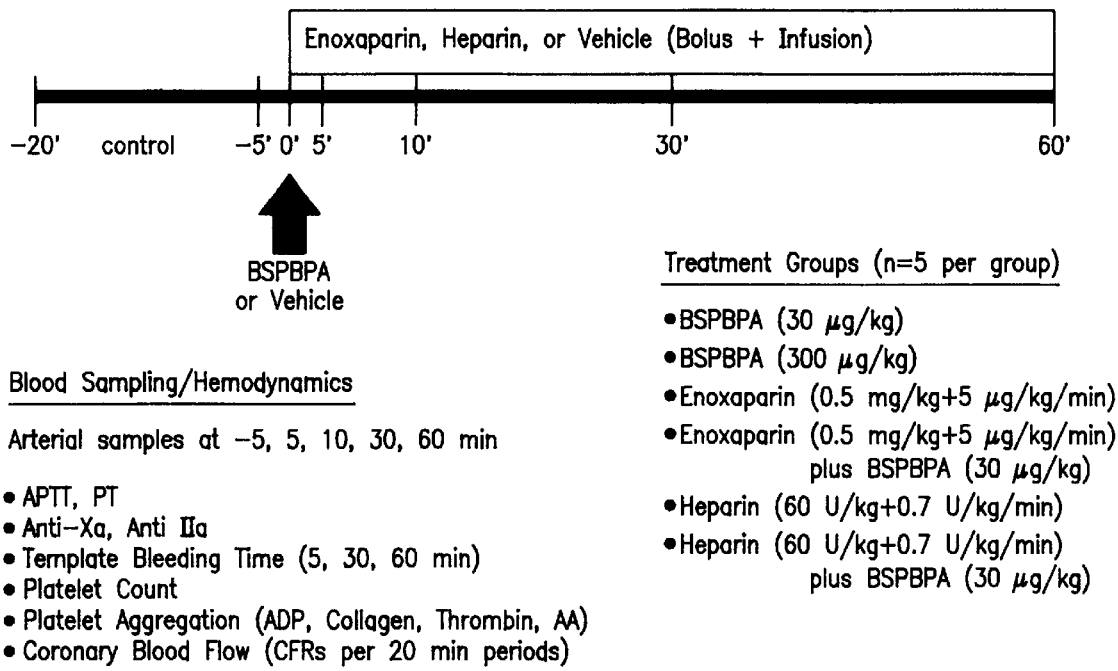
FIG. 1 represents information regarding assorted blood sampling/hemodynamic measurements during administration of different concentrations of the anti-Xa activity compound, Enoxaparin, the platelet aggregation antagonist compound, N-(n-butylsulfonyl)-4-(piperidin-4-ylbutyloxy)-L-phenylalanine (BSPBPA), and composition thereof over time.

As used above, and throughout the description of the invention, the following terms, unless otherwise indicated, shall be understood to have the following meanings:

Definitions

"Patient" includes both human and other mammals.

"Effective amount" is meant to describe an amount of composition according to the present invention effective in producing the desired therapeutic effect.

"Platelet aggregation antagonist compound" (PAAC) means a compound that binds to the platelet GPIIb/IIIa receptor (GPIIb/IIIa receptor antagonist) and competitively inhibits binding of fibrinogen, fibronectin and von Willebrand factor as well as inhibits aggregation of activated platelets.

"Anti-Xa activity compound" means a heparinoid compound or low molecular weight heparin (LMWH), or synthetic derivatives thereof.

Preferred Embodiments

According to a preferred embodiment of the invention, the following references, incorporated herein by reference, describes useful PAACs: Lynch et al. J. Pharm. Expt. Thera. 272(1) 20 (1995); Kereiakes et al. JACC 27(3), 536 (1996); Peerlinck et al. Circulation 88(4), 1512 (1993); Barrett et al. Clin. Pharmacol. Ther. 56(4) 377 (1994); Cook et al. Thromb. Haemostas. 70(5), 838 (1993); Plow, et al., Proc. Natl. Acad. Sci. USA 82, 8057–61 (1985); Ruggeri, et al., Proc. Natl. Acad. Sci. USA 5708–12 (1986); Ginsberg, et al., J. Biol. Chem. 260, 3931–36 (1985); and Gartner, et al., J. Biol. Chem. 260, 11,891–94 (1987); Plow, E. F., et al., Proc. Natl. Acad. Sci. USA 79, 3711–3715 (1982); Tjoeng, et al., U.S. Pat. Nos. 5,037,808, 4,879,313 and 4,992,463; Adams, et al., U.S. Pat. No. 4,857,508; Haverstick, D. M., et al., Blood 66(4), 946–952 (1985); Topol et al., The Lancet, 343, 881 (1994), French Application No. 86/17507; Zimmerman, et al., U.S. Pat. No. 4,683,291; European Application Publication No. 0 319 506; U.S. Pat. No. 5,023,233; U.S. Pat. No. 4,952,562; International Publication No. WO 91/04746; U.S. application Ser. No. 5,086,069; International Publication No. WO 92/13117; U.S. Pat. No. 5,053,392; U.S. Pat. No. 5,064,814; U.S. Pat. No. 5,051,405; European Patent Application 0479,481; European Patent Application 0478, 362; U.S. Pat. No. 5,292,756; International Publication No. WO 95/10295; and International Publication No. WO 89/11538. More preferred PAACs are those disclosed in International Publication No. WO 89/11538, International Publication No. WO 95/10295 or U.S. Pat. No. 5,292,756; further preferred are Reopro® (abciximab), N-[-[N-(4-(piperidin-4-yl)butanoyl)-N-ethylglycyl]aspartyl]-L-β-cyclohexyl alanine, N-[N[N-(4-(pperidin-4-yl)butanoyl)-N- ethylglycyl]aspartyl]-L-β-cyclohexyl alanine amide (PBGACA) or N-(n-butylsulfonyl)-4-(piperidin-4-ylbutyloxy)-L-phenylalanine (BSPBPA).

According to a preferred embodiment of the invention, the following references, incorporated herein by reference, describes useful LMWHs according to the invention and methods for preparing the LMWHs: Eur. Pat. No. 0014184; Medicinal Research Reviews 12(4), 373 (1992); Drugs of the Future 12(1), 45 (1987); International Publication No. WO 92/19249; U.S. Pat. No. 4,692,435; Barrowcliffe, Thromb. Res. 12, 27–36 (1977); Eur. Pat. Appln. No. 37319; Eur. Pat. Appln. No. 76279; U.S. Pat. No. 4,804,652: WO81/3276; Eur. Pat. Appln. No. 244235, Eur. Pat. Appln. No. 244236; U.S. Pat. No. 4,486,420; U.S. Pat. No. 4,692,435; U.S. Pat. No. 4,826,827; U.S. Pat. No. 3,766,167; Eur. Pat. Appln. No. 40144; Eur. Pat. Appln. No. 347588, Eur. Pat. Appln. No. 380943; U.S. Pat. No. 4533549; U.S. Pat. No. 4,629,699; Eur. Pat. Appln. No. 269981. For example, an anti-Xa activity compound may be produced as follows: enrichment by fractionation by ethanol and/or molecular sieving, e.g., gel filtration or membrane filtration of the LMWH present in standard heparin and controlled chemical (by nitrous acid, β-elimination or periodate oxidation) or enzymatic (by heparinases) depolymerization. The conditions for depolymerization can be carefully controlled to yield products of desired molecular weights. Nitrous acid depolymerization is commonly used. Also employed is depolymerization of the benzylic ester of heparin by β-elimination, which yields the same type of fragments as enzymatic depolymerization using heparinases. LMWH with low anticoagulant activity and retaining basic chemical structure are prepared by depolymerization using periodate oxidation or by removing the antithrombin-binding fraction of LMWH, or prepared by other methods, using immobilized antithrombin for adsorption.

Further preferred is a LMWH having an average molecular weight of about 3000 to about 6500. Commercially available LMWHs useful according to the invention include the following: Clexane®/Klexane®/Lovenox® (Enoxaparin (ENOX)) having an average molecular mass of 4500±1000 Dalton (Da), molecular mass distribution comprising components of <2000 Da (16.0±4.0%) and 2000 to 8000 Da (78.0±10.0%), Anti-Xa activity (IU/mg on dry basis) of 90 to 125, and an Anti-Xa/Anti-IIa ratio of 3.3 to 5.3; Fraxiparin® (Nardroparin) having an average molecular mass of 4300±700 Da, molecular mass distribution comprising components of <2000 Da (<15%), 2000 to 4000 Da (45±10%) and 2000 to 8000 Da (85±10%), Anti-Xa activity (IU/mg on dry basis) of 95 to 130, and an Anti-Xa/Anti-IIa ratio of 2.5 to 4.0; Fragmin® (Dalteparin) having an average molecular mass of 6000±400 Da, molecular mass distribution comprising components of <3000 Da (5.0 to 13.0%) and >8000 Da (15.0 to 25.0%), Anti-Xa activity (IU/mg on dry basis) of 110 to 210, and an Anti-Xa/Anti-IIa ratio of 1.9 to 3.2; Embolex®/Monoembolex® (Certroparin) having an average molecular mass of 5200±1000 Da, molecular mass distribution comprising components of <2000 Da (10 to 25%) and <8000 Da (75 to 90%), Anti-Xa activity (IU/mg on dry basis) of 80 to 120, and an Anti-Xa/Anti-IIa ratio of 1.5 to 2.5; Fluxum®/Minidalton®/Lowhepa® (Parnaparin) having an average molecular mass of 5000±1000 Da, molecular mass distribution comprising components of <3000 Da (20 to 30%) and 3000 to 8000 Da (50 to 60%), Anti-Xa activity (IU/mg on dry basis) of 75 to 110, and an Anti-Xa/Anti-IIa ratio of 2.0 to 3.0; Logiparin® (Tinzaparin) having an average molecular mass of 3400 to 5600 Da, molecular mass distribution comprising components of <2000 Da (2.0 to 16.0%), 2000 to 4000 Da (66.0±6.0%) and >8000 Da (12.0 to 38.0%), Anti-Xa activity (IU/mg on dry basis) of >70, and an Anti-Xa/Anti-IIa ratio of 1.5 to 2.5; Clivarine® (Reviparin) and Normiflo® (ardeparin/RD heparin/RDH). A preferred LMWH according to the invention is prepared according to the procedures disclosed in U.S. Pat. No. 4,486,420 or U.S. Pat. No. 4,692,435; more preferred enoxaparin.

According to another preferred embodiment of the invention, an anti-Xa activity compound is a heparinoid compound. The following references, incorporated herein by reference, describe a useful heparinoid compound according to the invention and methods for preparing the heparinoid compound: U.S. Pat. No. 4,438,108, Eur. Pat. No. EP 66908, Zammit et al. Thromb. Haemostas. 71(6), 759 (1994), and Gent et at. Circulation 93, 80 (1996). A preferred commercially available heparinoid compound useful according to the invention is Orgaran® (Danaparoid) having an average molecular mass of about 6500 Da, Anti-Xa activity (IU/mg on dry basis) of about 10, and an Anti-Xa/Anti-IIa ratio of about 28.

Preferred thrombogenic conditions treatable or preventable according to the invention include stroke, atherosclerosis, angiogenesis, thrombosis, thromboembolic conditions such as deep venous thrombosis, pulmonary embolism or thrombophlebitis, disseminated intravascular coagulation or thromboembolic syndromes associated with cancer, sepsis or obstetrical complications, peripheral arterial occlusive disease, and acute coronary syndromes such as unstable angina and myocardial infarction, hemodialysis, or extra-corporeal circulation requirement associated with a surgical procedure or tissue damage caused by phospholipases A2 ($PLA_2$); more preferred is unstable angina and myocardial infarction.

Another preferred embodiment according to the invention useful in the course of a medical procedure wherein there is a potential for an occurrence pathological thrombogenic condition may occur, such as during coronary artery bypass surgery or percutaneous transluminal coronary angioplasty with or without placement of an intracoronary stent; more preferred is percutaneous transluminal coronary angioplasty with or without placement of an intracoronary stent.

Another preferred embodiment according to the invention is the use of pharmaceutically effective amounts of a compound having anti-Xa activity and a platelet aggregation antagonist compound in the preparation of a inedicament for treating or preventing a physiological condition associated with thrombosis related ischemic disorder.

In the treatment or prevention method according to the invention the anti-Xa activity compound and platelet aggregation antagonist compound may be administered in different ways, such as in combination therapies optionally employing medical procedures. For example, the anti-Xa activity compound and platelet aggregation antagonist compound may be administered to a patient concomitantly or at different times provided that they are administered such that at some period of time there are pharmaceutically effective amounts of both compounds present in the patient such that a therapeutic effect according to the invention results.

Thus, it is a further object of the invention to provide a kit for treating or preventing a physiological condition associated with thrombosis related ischemic disorder, said kit comprising a plurality of separate containers, wherein at least one of said containers contains a compound having anti-Xa activity and at least another of said containers contains a platelet aggregation antagonist compound, and said containers optionally contain a pharmaceutical carrier, which kit may be effectively utilized for carrying out combination therapies according to the invention. A further embodiment for a kit would be wherein of said containers at least one of said containers should contain the compound having anti-Xa activity without the presence of the platelet aggregation antagonist compound, and at least another of said containers should contain the platelet aggregation antagonist compound without the presence of the compound having anti-Xa activity.

In practice, the anti-Xa activity compound and platelet aggregation antagonist compound may be administered parenterally, topically, rectally, transdermally, intrapulmonary or orally, but they are preferably administered parenterally and/or orally.

Suitable compositions containing the compounds used according to the invention may be prepared by conventional means. For example, the compounds used according to the invention may be dissolved or suspended in a suitable carrier.

The compounds used according to the invention should be presented in forms permitting administration by the most suitable route, and the invention also relates to a pharmaceutical composition containing the compounds used according to the invention which are suitable for use in human or veterinary medicine. These compositions may be prepared according to the customary methods, using one or more pharmaceutically acceptable carrier, which comprise adjuvants or excipients. The adjuvants comprise, inter alia, diluents, sterile aqueous media and the various non-toxic organic solvents. The compositions may be presented in the form of tablets, pills, capsules, lozenges, troches, hard candies, granules, powders, aqueous solutions or suspensions, injectable solutions, elixirs or syrups, powders, solution or suspension for intrapulmonary administration and can contain one or more agents chosen from the group comprising sweeteners, flavorings, colorings, or stabilizers in order to obtain pharmaceutically acceptable preparations.

The choice of vehicle and the content of compounds used according to the invention in the vehicle are generally determined in accordance with the solubility and chemical properties of the compounds, the particular mode of administration and the provisions to be observed in pharmaceutical practice. For example, excipients such as sterile water, Ringer's solution, lactose, sodium citrate, isotonic saline solutions (monosodium or disodium phosphate, sodium, potassium, calcium or magnesium chloride, or mixtures of such salts), calcium carbonate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the compounds used according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are useful. The solutions of the salts of the compounds used according to the invention are especially useful for administration by intramuscular, intravenous, intraarterial or subcutaneous injection or infusion techniques. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

The anti-Xa activity compound and platelet aggregation antagonist compound according to the invention may also be formulated in a manner which resists rapid clearance from the vascular (arterial or venous) wall by convection and/or diffusion, thereby increasing the residence time of the composition at the desired site of action. Depot useful according to the invention may be in a copolymer matrix, such as ethylene-vinyl acetate, or a polyvinyl alcohol gel surrounded by a Silastic shell. Alternatively, the anti-Xa activity compound and platelet aggregation antagonist compound may be delivered locally from a silicone polymer implanted in the adventitia.

An alternative approach for minimizing washout of the anti-Xa activity compound and platelet aggregation antagonist compound during percutaneous, transvascular delivery comprises the use of nondiffusible, drug-eluting microparticles. The microparticles may be comprised of a variety of synthetic polymers, such as polylactide for example, or natural substances, including proteins or polysaccharides. Such microparticles enable strategic manipulation of variables including total dose of a drug and kinetics of its release. Microparticles can be injected efficiently into the arterial or venous wall through a porous balloon catheter or a balloon over stent, and are retained in the vascular wall and the periadventitial tissue for at least about two weeks. Formulations and methodologies for local, intravascular site-specific delivery of therapeutic agents are discussed in Reissen et al. (J. Am. Coll. Cardiol. 1994; 23: 1234–1244), the entire contents of which are hereby incorporated by reference.

The medium for the anti-Xa activity compound and platelet aggregation antagonist compound can also be a hydrogel which is prepared from any biocompatible or non-cytotoxic (homo or hetero) polymer, such as a hydrophilic polyacrylic acid polymer that can act as a drug absorbing sponge. Such polymers have been described, for example, in application WO93/08845, the entire contents of which are hereby incorporated by reference. Certain of them, such as, in particular, those obtained from ethylene and/or propylene oxide are commercially available.

In addition, the anti-Xa activity compound and platelet aggregation antagonist compound may be administered directly to the blood vessel wall by means of an angioplasty balloon which is coated with a hydrophilic film (for example a hydrogel), or by means of any other catheter containing an infusion chamber for the compounds, which can thus be applied in a precise manner to the site to be treated.

The percentage of the anti-Xa activity compound and platelet aggregation antagonist compound used according to the invention may be varied. The compounds should constitute a proportion such that a suitable dosage shall be obtained. Obviously, several unit dosage forms may be administered. The dose employed will be detennined by the physician, and depends upon the desired therapeutic effect, the route of administration and the duration of the treatment, and the condition of the patient. In each particular case, the doses will be detennined in accordance with the factors distinctive to the subject to be treated, such as age, weight, general state of health and other characteristics which can influence the efficacy of the medicinal product.

In the adult, the dosages of the PAAC are generally from about 0.0001 to about 50, preferably about 0.0001 to about 5, mg/kg body weight per day by inhalation, from about 0.001 to about 100, preferably 0.01 to 70, more especially 0.05 to 10, mg/kg body weight per day by oral administration, and from about 0.0001 to about 10, preferably 0.001 to 1, mg/kg body weight per day by intravenous administration.

In the adult, the dosages of the anti-Xa activity compound according to the invention is particularly useful in doses of about 10 to about 25,000 international units of anti-Xa activity.

The anti-Xa activity compound and platelet aggregation antagonist compound used according to the invention may be administered as frequently as necessary in order to obtain the desired therapeutic effect. The dosage regimen in carrying out the method of this invention is that which insures maximum therapeutic response until improvement is obtained and thereafter the minimum effective level which gives relief. Some patients may respond rapidly to a higher or lower dose and may find much weaker maintenance doses adequate. Both short- and long-term treatments regimens are contemplated for the invention. Treatments at the rate of about 1 to about 4 doses per day are also contemplated, in accordance with the physiological requirements of each particular patient, bearing in mind, of course, that in selecting the appropriate dosages in any specific case, consideration must be given to the patient's weight, general health, age, and other factors which may influence response to the drug. Thus, for other patients, it will be necessary to prescribe not more than one or two doses per day.

The compounds of the present invention may also be formulated for use in conjunction with other therapeutic agents such as agents or in connection with the application of therapeutic techniques to address pharmacological conditions which may be ameliorated through the application of a compound of formula I, such as in the following:

The compounds of the present invention may be used in the treatment of restenosis post angioplasty using any device such as balloon, ablation or laser techniques. The compounds of the present invention may be used in the treatment of restenosis following stent placement in the vasculature either as 1) primary treatment for vascular blockage, or 2) in the instance where angioplasty using any device fails to give a patent artery. The compounds of the present invention may be used either orally, by parenteral administration or the compound could be applied topically through the intervention of a specific device or as a properly formulated coating on a stent device.

The compounds of the present invention may be used in the treatment of restenosis in combination with any anticoagulant, antiplatelet, antithrombotic or profibrinolytic agent. Often patients are concurrently treated prior, during and after interventional procedures with agents of these classes either in order to safely perform tile interventional procedure or to prevent deleterious effects of thrombus fonmation. Some examples of classes of agents known to be anticoagulant, antiplatelet, antithrombotic or profibrinolytic agents include any formulation of thrombin inhibitors or Factor VIIa inhibitors. Some examples of classes of agents known to be anticoagulant, antiplatelet, antitlirombotic or profibrinolytic agents include any formulation of aspirin, direct thrombin inhibitors, direct Factor Xa inhibitors, or Factor VIIa inhibitors.

The compounds of the present invention may be used in combination with any antihypertensive agent or cholesterol or lipid regulating agent in the treatment of restenosis or atherosclerosis concurrently with the treatment of high blood pressure or atherosclerosis. Some examples of agents that are useful in the treatment of high blood pressure include compounds of the following classes; beta-blockers, ACE inhibitors, calcium channel antagonists and alpha-receptor antagonists. Some examples of agents that are useful in the treatment of elevated cholesterol levels or disregulated lipid levels include compounds known to be HMGCoA reductase inhibitors, compounds of the fibrate class, The anti-Xa activity compound and platelet aggregation antagonist compound used according to the invention exhibit marked pharmacological activities according to tests described in the literature which tests results are believed to correlate to pharmacological activity in humans and other mammals. The following pharmacological test results are typical characteristics of the anti-Xa activity compound and platelet aggregation antagonist compound used according to the invention.

Figure 2:
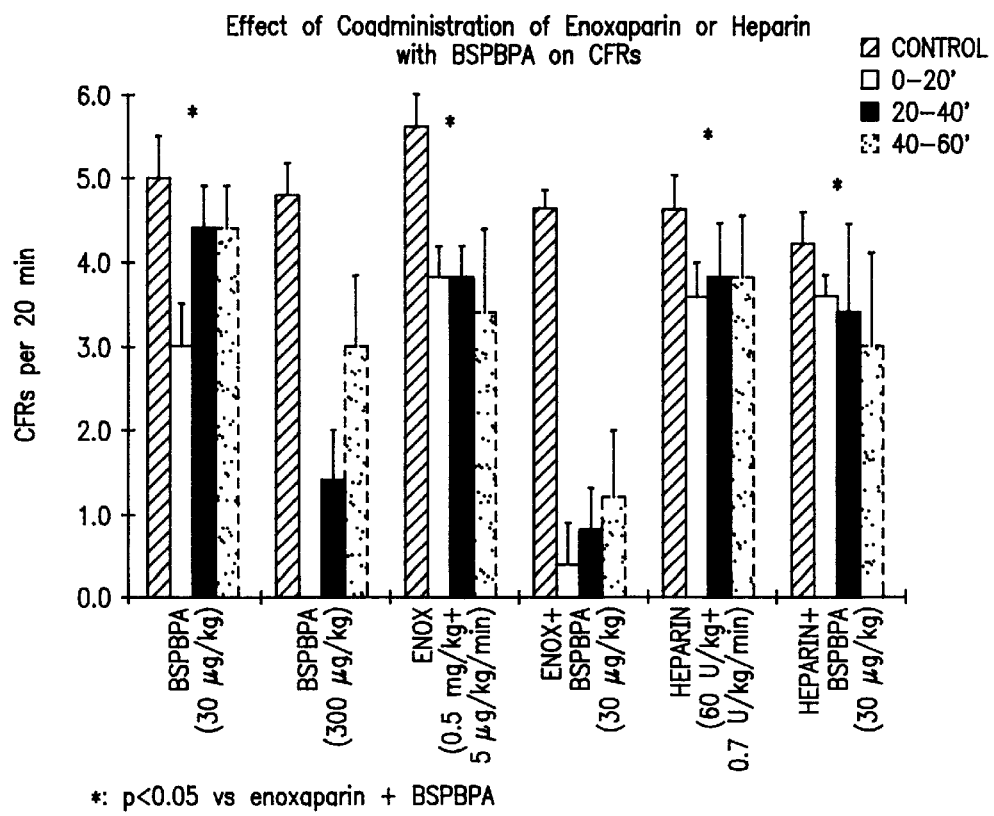
FIG. 2 represents a graph of the number of cyclic flow reductions (CFRs) for different concentrations of the anti-Xa activity compound, Enoxaparin, the platelet aggregation antagonist compound, BSPBPA, and composition thereof over time.
Figure 3:
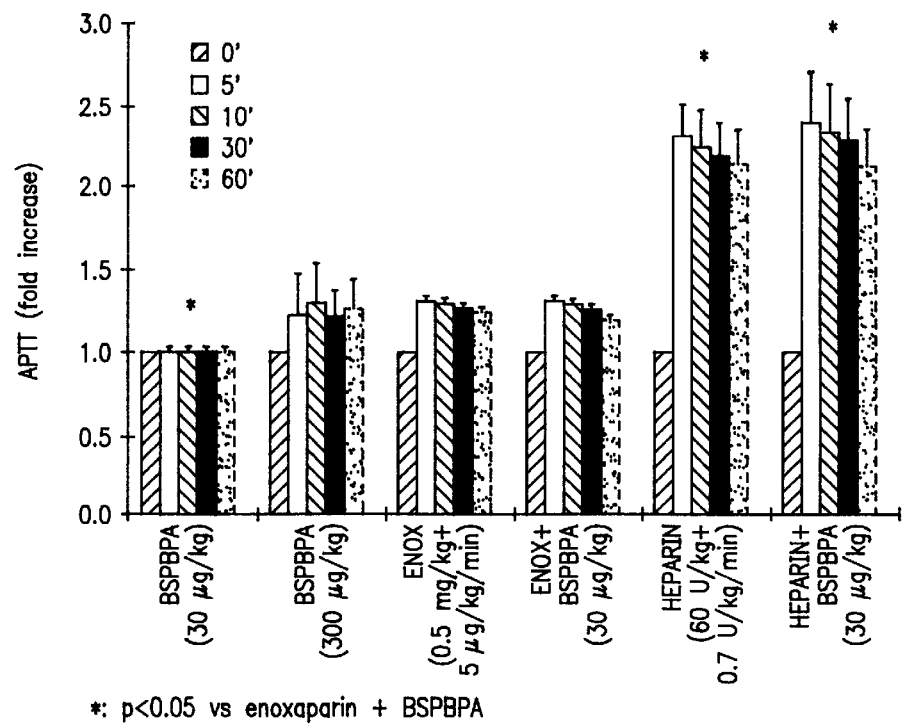
FIG. 3 represents a graph of the activated partial thromboplastin time (APTT) for different concentrations of the anti-Xa activity compound, Enoxaparin, the platelet aggregation antagonist compound, BSPBPA, and composition thereof over time.
Figure 4:
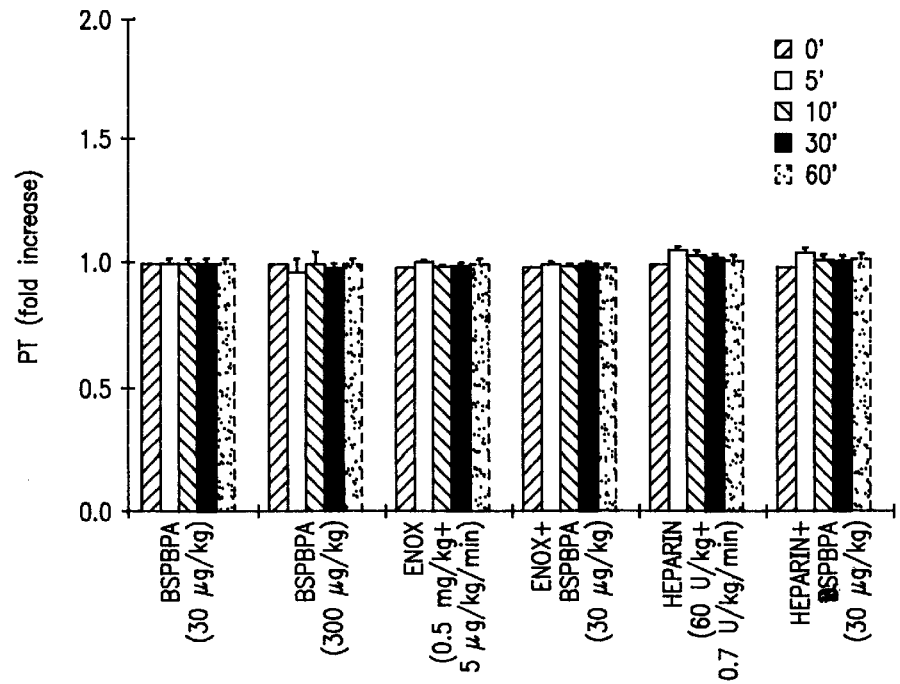
FIG. 4 represents a graph of the prothrombin time (PT) for different concentrations of the anti-Xa activity compound, Enoxaparin, the platelet aggregation antagonist compound, BSPBPA, and composition thereof over time.
Figure 5:
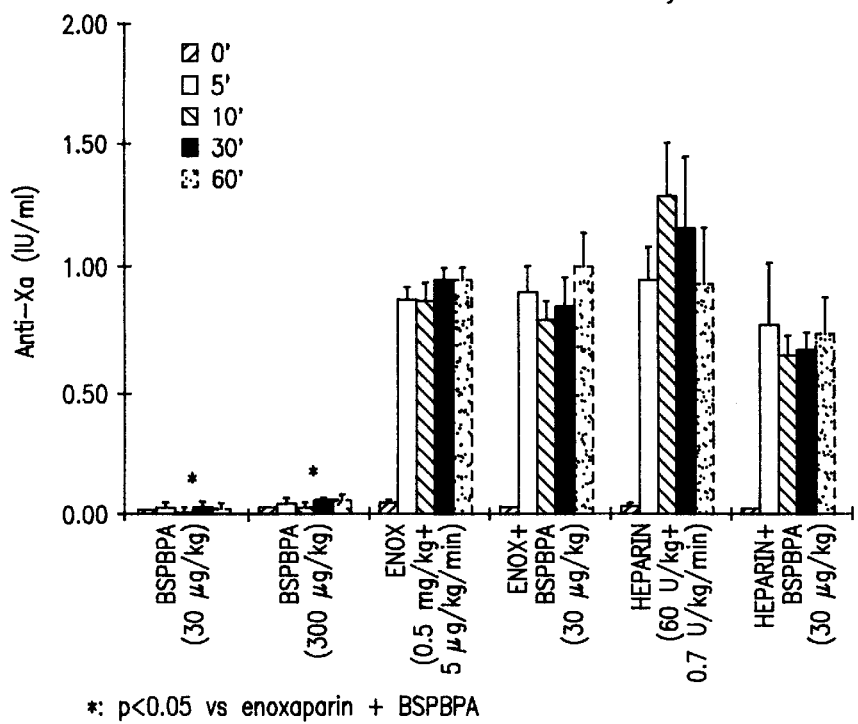
FIG. 5 represents a graph of the Anti-Xa activity for different concentrations of the anti-Xa activity compound, Enoxaparin, the platelet aggregation antagonist compound, BSPBPA, and composition thereof over time.
Figure 6:
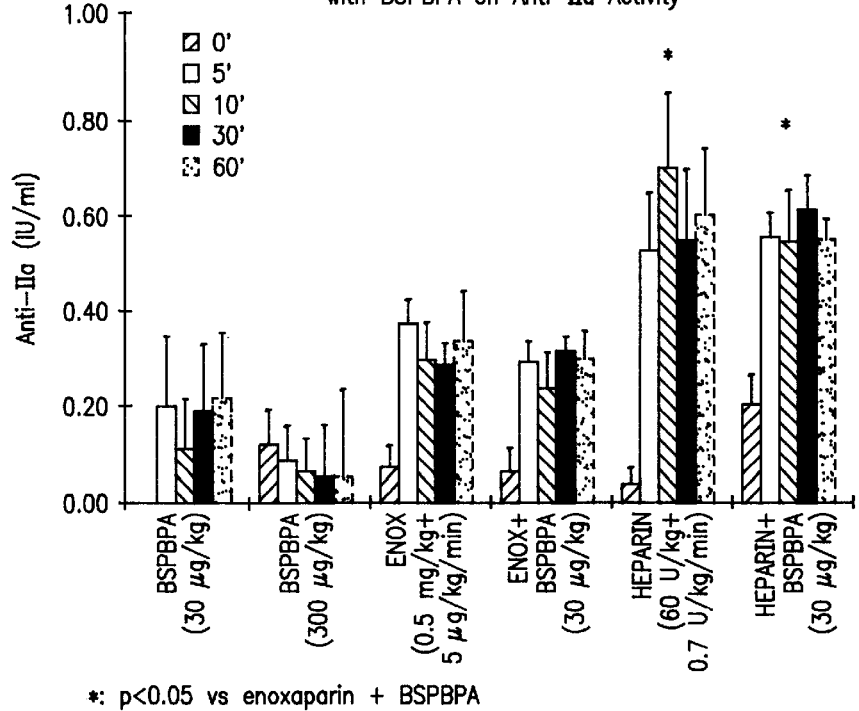
FIG. 6 represents a graph of the Anti-IIa activity for different concentrations of the anti-Xa activity compound, Enoxaparin, the platelet aggregation antagonist compound, BSPBPA, and composition thereof over time.
Figure 7:
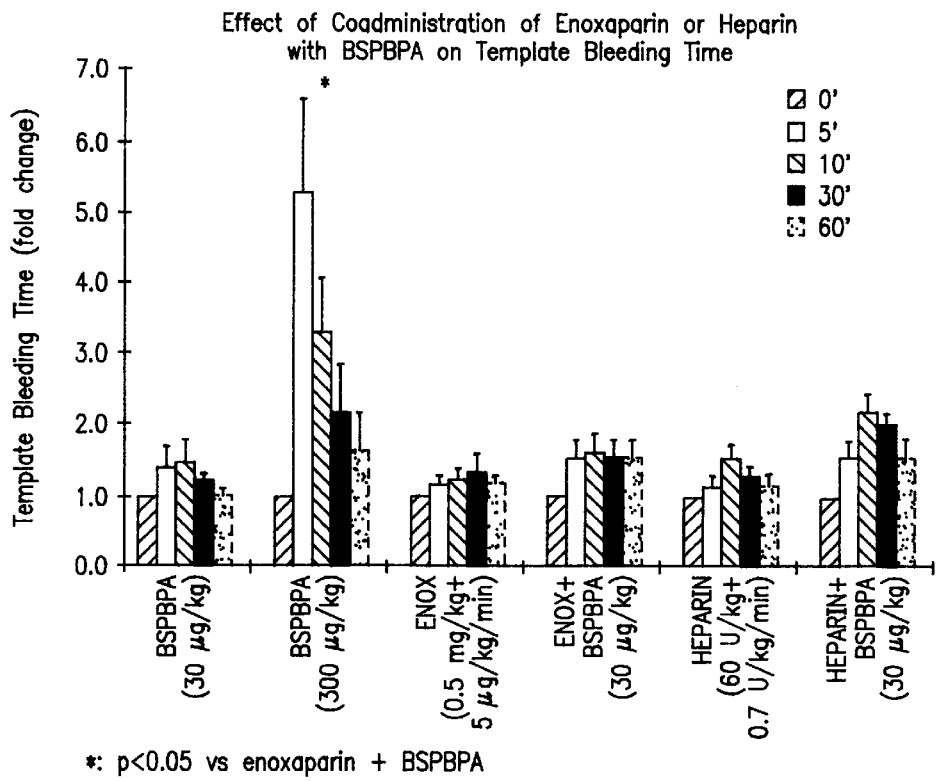
FIG. 7 represents a graph of the template bleeding time for different concentrations of the anti-Xa activity compound, Enoxaparin, the platelet aggregation antagonist compound, BSPBPA, and composition thereof over time.
Figure 8:
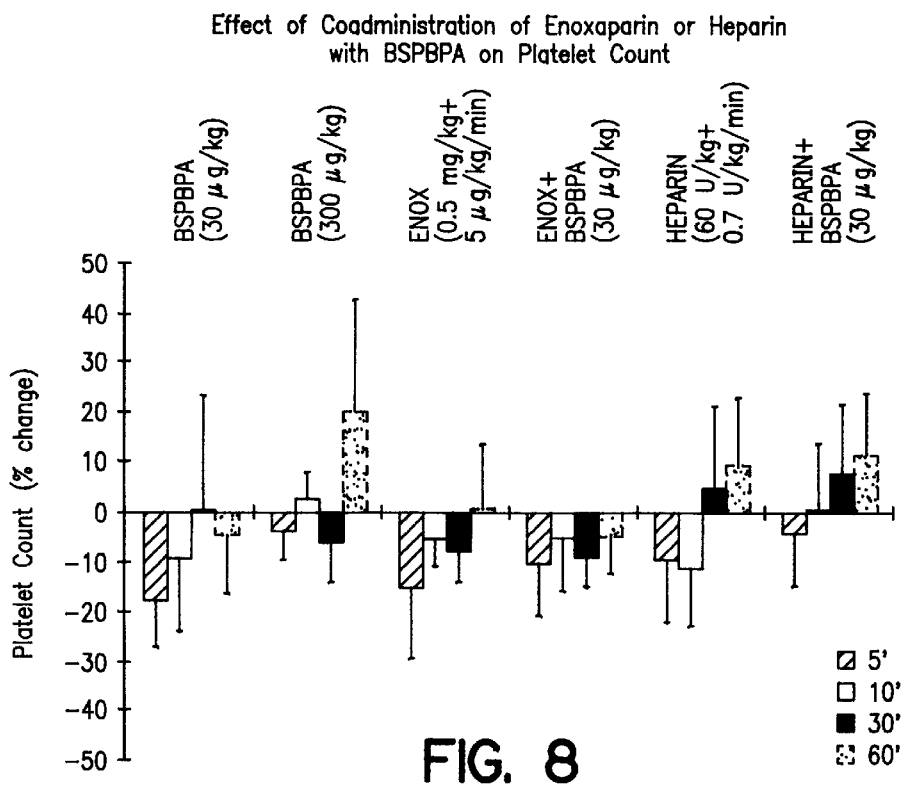
FIG. 8 represents a graph of the platelet count for different concentrations of the anti-Xa activity compound, Enoxaparin, the platelet aggregation antagonist compound, BSPBPA, and composition thereof over time.
Figure 9:
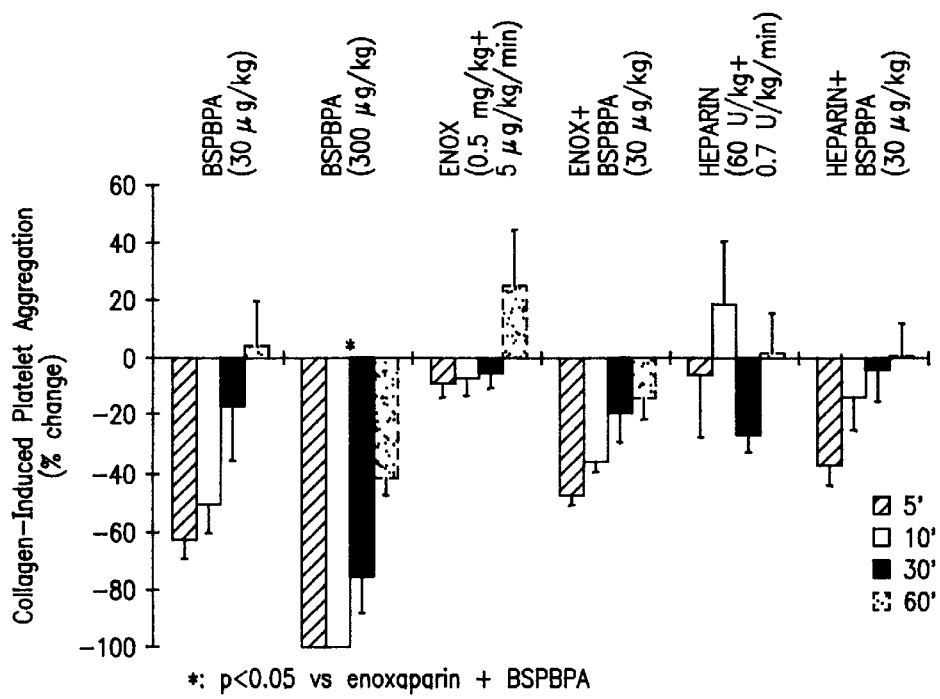
FIG. 9 represents a graph of collagen-induced ex-vivo platelet aggregation for different concentrations of the anti-Xa activity compound, Enoxaparin, the platelet aggregation antagonist compound, BSPBPA, and composition thereof over time.
Figure 10:
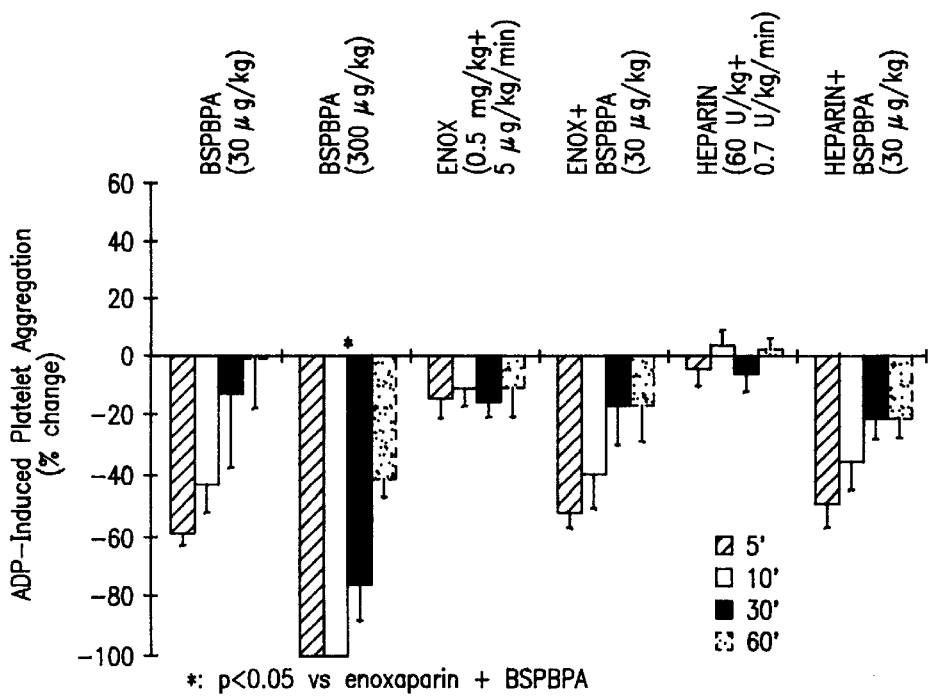
FIG. 10 represents a graph of ADP-induced ex-vivo platelet aggregation for different concentrations of the anti-Xa activity compound, Enoxaparin, the platelet aggregation antagonist compound, BSPBPA, and composition thereof over time.
Figure 11:
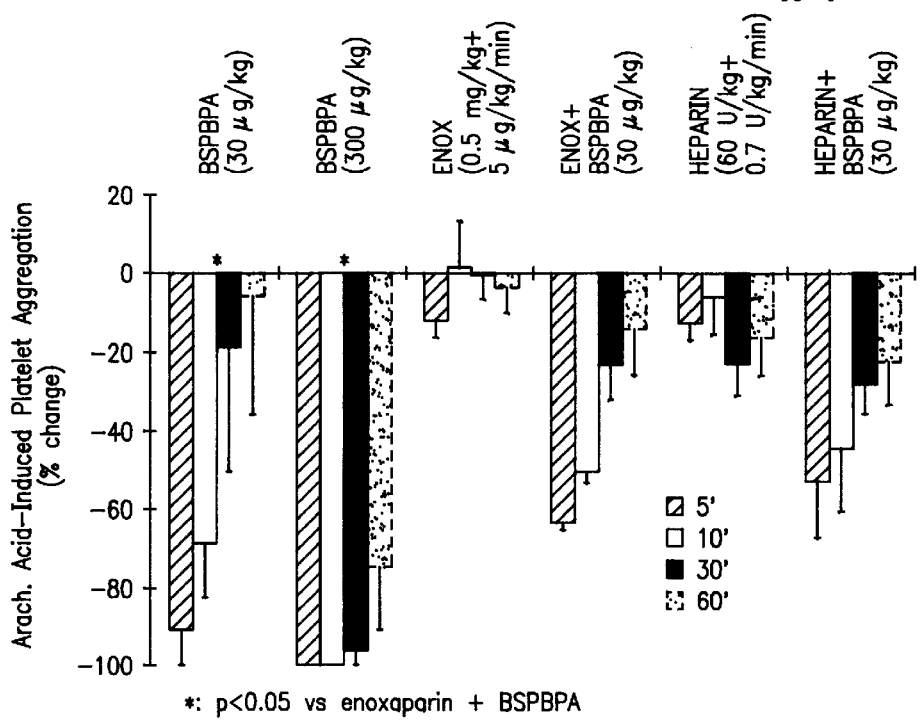
FIG. 11 represents a graph of arachidonic acid-induced ex-vivo platelet aggregation for different concentrations of the anti-Xa activity compound, Enoxaparin, the platelet aggregation antagonist compound, BSPBPA, and composition thereof over time.
Figure 12:
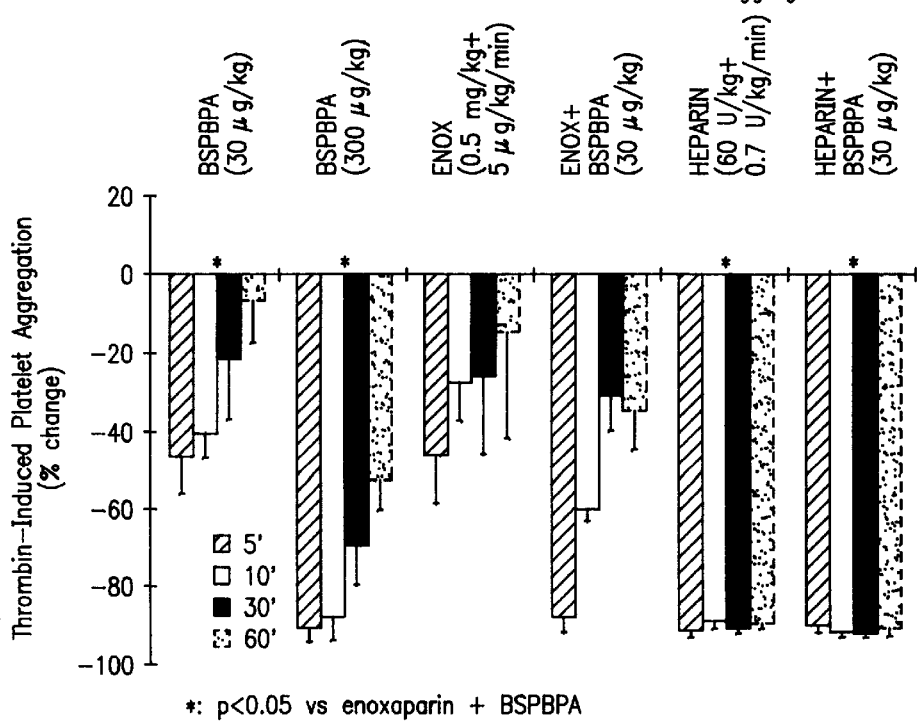
FIG. 12 represents a graph of thrombin-induced ex-vivo platelet aggregation for different concentrations of the anti-Xa activity compound, Enoxaparin, the platelet aggregation antagonist compound, BSPBPA, and composition thereof over time.
Figure 15:
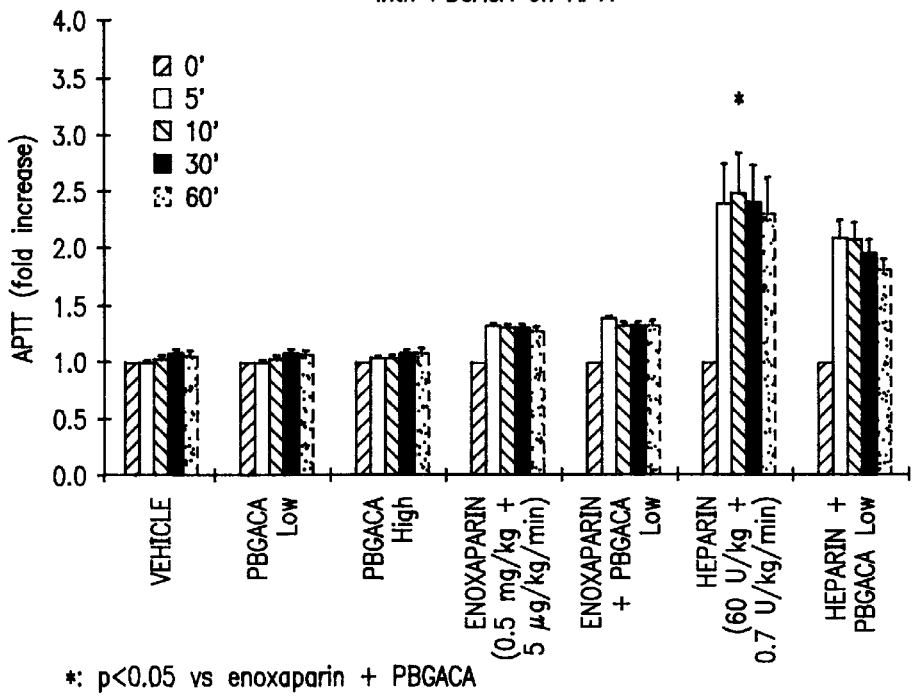
FIG. 15 represents a graph of the activated partial thromboplastin time (APTT) for different concentrations of the anti-Xa activity compound, Enoxaparin, the platelet aggregation antagonist compound, PBGACA, and composition thereof over time.
Figure 16:
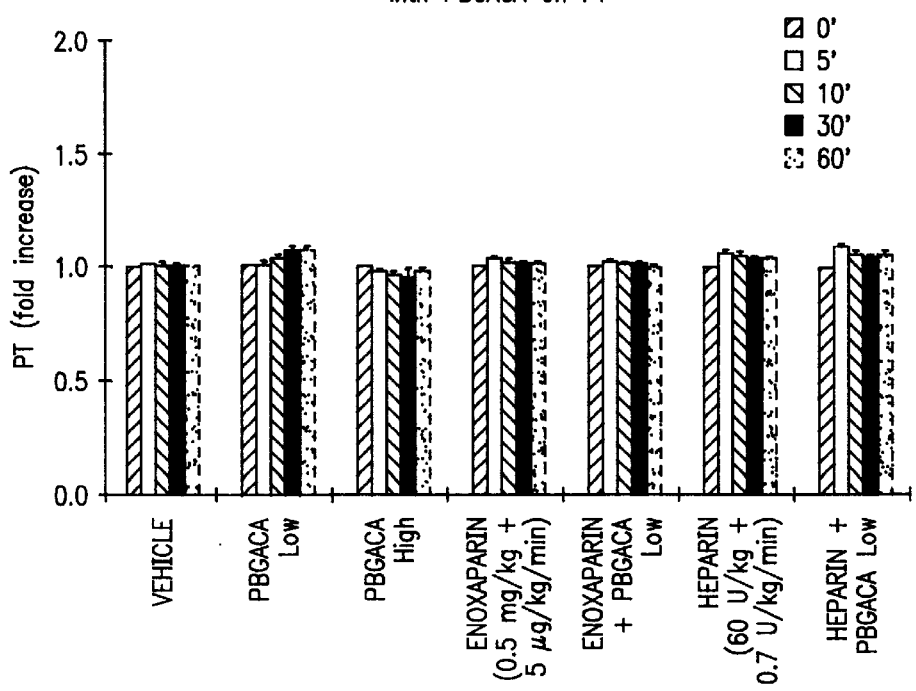
FIG. 16 represents a graph of the prothrombin time (PT) for different concentrations of the anti-Xa activity compound, Enoxaparin, the platelet aggregation antagonist compound, PBGACA, and composition thereof over time.
Figure 17:
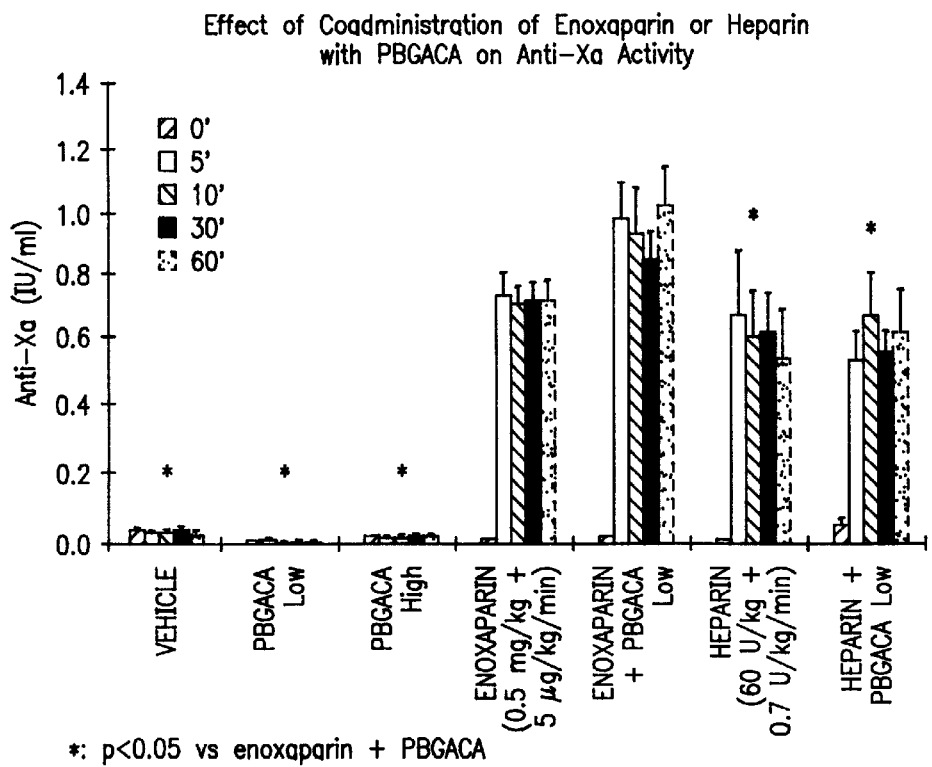
FIG. 17 represents a graph of the Anti-Xa activity for different concentrations of the anti-Xa activity compound, Enoxaparin, the platelet aggregation antagonist compound, PBGACA, and composition thereof over time.
Figure 18:
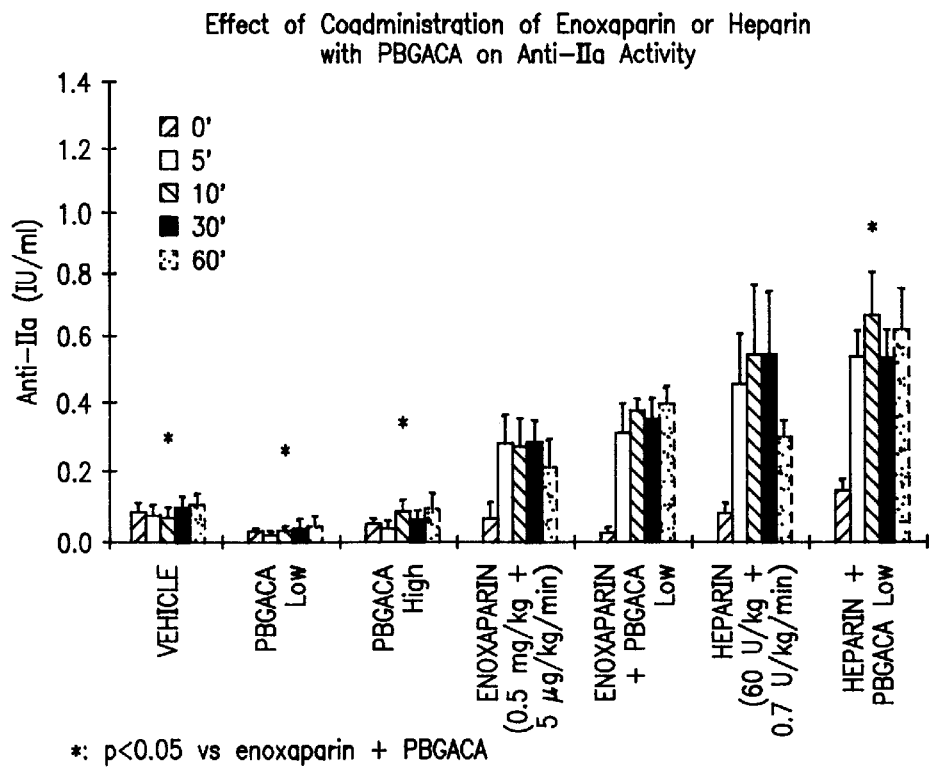
FIG. 18 represents a graph of the Anti-IIa activity for different concentrations of the anti-Xa activity compound, Enoxaparin, the platelet aggregation antagonist compound, PBGACA, and composition thereof over time.
Figure 19:
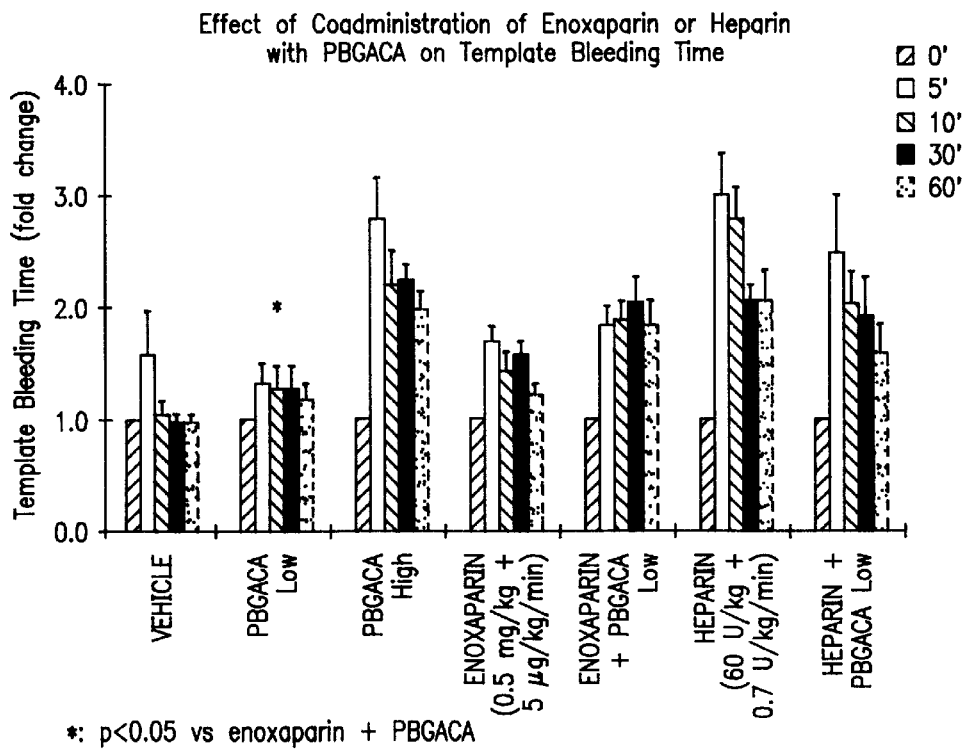
FIG. 19 represents a graph of the template bleeding time for different concentrations of the anti-Xa activity compound, Enoxaparin, the platelet aggregation antagonist compound, PBGACA, and composition thereof over time.
Figure 20:
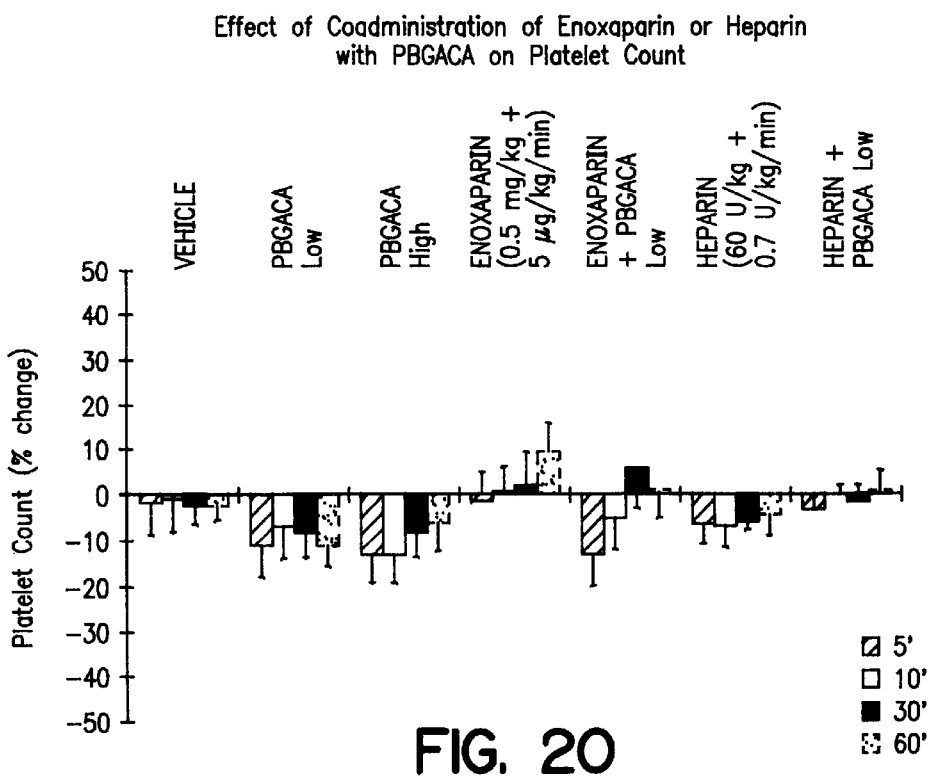
FIG. 20 represents a graph of the platelet count for different concentrations of the anti-Xa activity compound, Enoxaparin, the platelet aggregation antagonist compound, PBGACA, and composition thereof over time.
Figure 21:
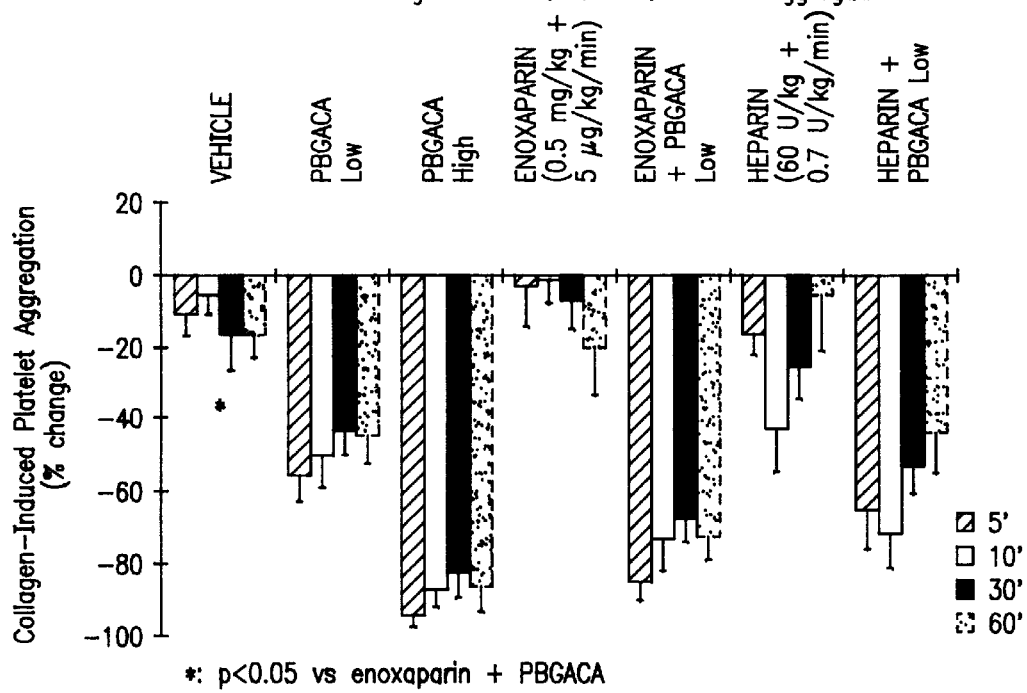
FIG. 21 represents a graph of collagen-induced ex-vivo platelet aggregation for different concentrations of the anti-Xa activity compound, Enoxaparin, the platelet aggregation antagonist compound, PBGACA, and composition thereof over time.
Figure 22:
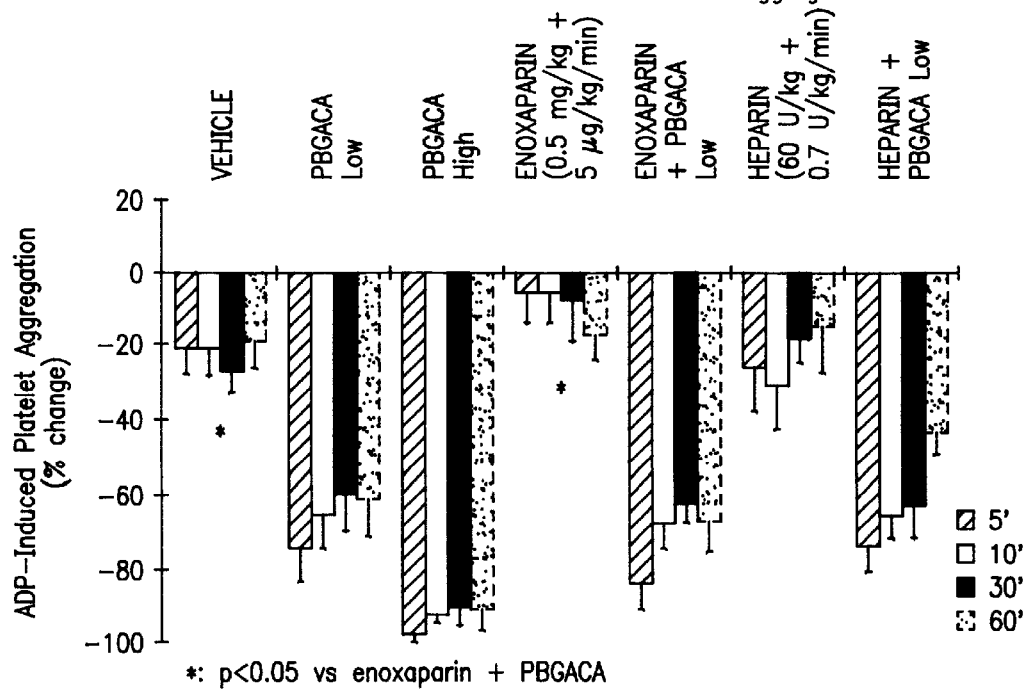
FIG. 22 represents a graph of ADP-induced ex-vivo platelet aggregation for different concentrations of the anti-Xa activity compound, Enoxaparin, the platelet aggregation antagonist compound, PBGACA, and composition thereof over time.
Figure 23:
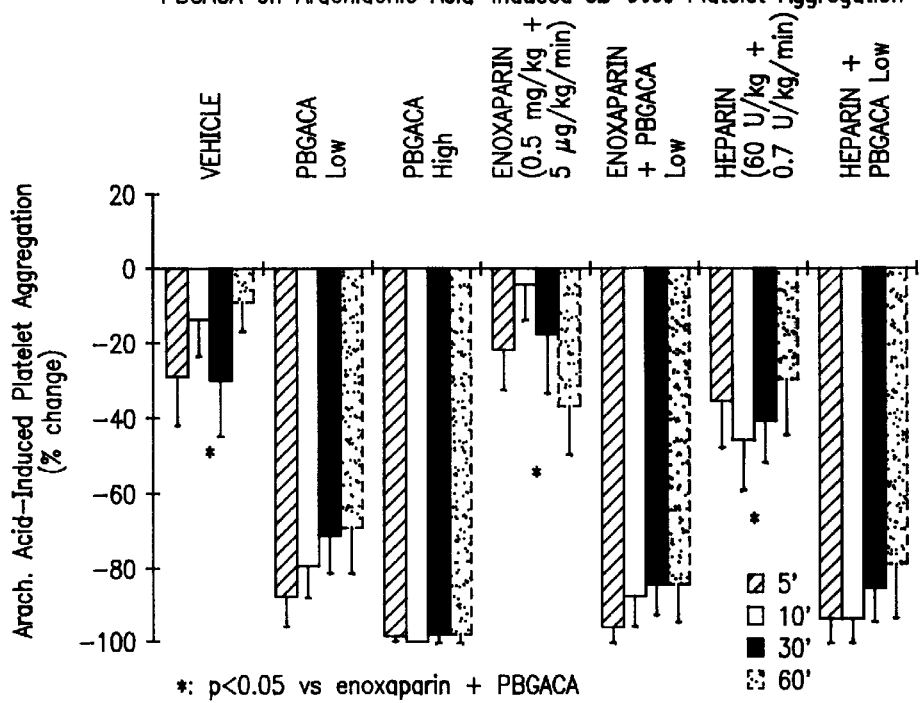
FIG. 23 represents a graph of arachidonic acid-induced ex-vivo platelet aggregation for different concentrations of the anti-Xa activity compound, Enoxaparin, the platelet aggregation antagonist compound, PBGACA, and composition thereof over time.
Figure 24:
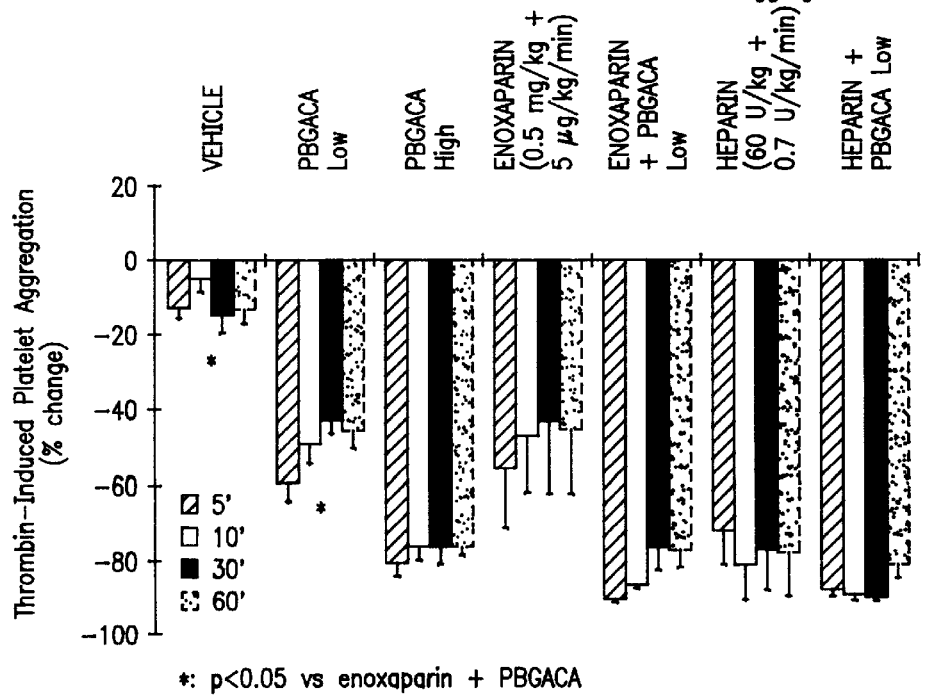
FIG. 24 represents a graph of thrombin-induced ex-vivo platelet aggregation for different concentrations of the anti-Xa activity compound, Enoxaparin, the platelet aggregation antagonist compound, PBGACA, and composition thereof over time.

The following pharmacological tests evaluate the activity of anti-Xa activity compound and platelet aggregation antagonist compound used according to the invention. Those tests include the hemodynamics measurements during administration of different concentrations of an anti-Xa activity compound, a platelet aggregation antagonist compound and composition thereof over time (FIGS. 1 and 13). More specifically measurements were taken of cyclic flow reduction (FIGS. 2 and 14), activated partial thromboplastin time (FIGS. 3 and 15), prothrombin time (FIGS. 4 and 16), Anti-Xa activity (FIGS. 5 and 17), Anti-IIa activity (FIGS. 6 and 18), template bleeding time (FIGS. 7 and 19), platelet count (FIGS. 8 and 20), collagen-induced ex-vivo platelet aggregation (FIGS. 9 and 21), ADP-indticed ex-vivo platelet aggregation (FIGS. 10 and 22), arachidonic acid-induced ex-vivo platelet aggregation (FIGS. 11 and 23), and thrombin-induced ex-vivo platelet aggregation (FIGS. 12 and 24).

Compositions of the present invention exhibit marked activity in the foregoing tests and are considered useful in the prevention and treatment of thrombosis associated with certain disease states. Antithrombotic activity in the ex vivo canine platelet aggregation assay is predictive of such activity in humans (see, for example, Catalfamo, J. L., and Dodds, W. Jean, "Isolation of Platelets from Laboratory Animals", Methods Enzymol. 169, Part A, 27 (1989)).

Materials and Methods

All procedures in this study are performed in compliance with the Animal Welfare Act Regulations and with the Guide for the Care and Use of Laboratory Animals (DHEW Publication No. NIH 85–23, 1985).

The test protocol as follows is an experimental model of unstable angina.

Mongrel dogs of either sex (15–21 kg) are anesthetized with sodium pentobarbital (30 mg/kg, i.v., with supplements given as needed), intubated, and ventilated using a Harvard respirator (Harvard Apparatus. S. Natick, Mass.). A tri-lumen catheter (SAFEDWELLplus, Becton Dickinson, Sandy, Utah) is placed in the right femoral vein for the administration of test agents and supplemental anesthesia. The right femoral artery is cannulated for measurement of arterial blood pressure and for obtaining blood samples.

A left thoracotomy is performed at the 5th intercostal space and the heart is suspended in a pericardial cradle. The left circumflex coronary artery (LCX) is isolated and dissected for a distance of 2 cm, ligating side branches when necessary. An electromagnetic flow probe (Carolina Medical Electronics, 501D) is placed on the vessel to monitor coronary blood flow and a snare ligature is placed on the distal portion of the vessel to produce a temporary mechanical occlusion which is used to aid in adjusting the degree of stenosis and to aid in validating zero flow measurements.

Distal to the flow probe, a Lexan® occluder is positioned for the purpose of creating a critical stenosis, which is confirmed by abolishment of the hyperemic response to a 10 sec mechanical occlusion of the vessel. The endothelium and vascular smooth muscle cells are damaged by compressing the vessel with a vascular clamp. These conditions result in platelet adhesion and aggregation at the damaged area, thus producing a gradual decrease in coronary blood flow. When flow reaches zero, the occluder is moved back and forth over the damaged area to mechanically dislodge the platelet-rich thrombus, thus restoring blood flow. This repetitive pattern of decreasing blood flow that is restored by mechanical disruption of the platelet thrombus is referred to as cyclic flow reductions (CFRs). The antithrombotic effect of the test agents is quantitated by comparing the number of CFRs that occurred during a 20 min control period with the number of CFRs per 20 min for three consecutive 20 min periods after drug administration. A significant reduction in the number of CFRs is taken to represent an antitlirombotic effect.

Experimental Protocol a. Protocol using BSPBPA

Thirty dogs are assigned to one of six adjunctive treatment groups. The compounds are administered as an intravenous bolus only (for N-(n-butylsulfonyl)-4-(piperidini-4-ylbutyloxy)-L-phenylalanine (BSPBPA) or saline vehicle) or as an intravenous bolus plus a constant intravenous infusion (for heparin, enoxaparin (ENOX), or saline vehicle. The treatment groups are: I) BSPBPA (30 μg/kg), II) BSPBPA (300 μ/kg), III) ENOX (0.5 mg/kg+5 μg/kg/min) IV) ENOX (0.5 mg/kg+5 μg/kg/min) plus BSPBPA (30 μg/kg), V) heparin (60 U/kg+0.7 U/kg/min), and VI) heparin (60 U/kg+0.7 U/kg/min) plus BSPBPA (30 μg/kg). All compounds are diluted in saline and bolus injections are made using a volume of 5 mL and constant infusions are made using a volume of 22 mL.

a. Protocol using PBGACA

Thirty dogs are assigned to one of six adjunctive treatment groups. The compounds for these experiments involves the administration of the following agents as a bolus and a constant infusion (for N-[N[N-(4-(piperidin-4-yl)butanoyl)-N-ethylglycyl]aspartyl]-L-β-cyclohexyl alanine amide (PBGACA) or saline vehicle) or as an intravenous bolus plus a constant intravenous infusion (for heparin, ENOX, or saline vehicle. The treatment groups were: I) PBGACA (10 μg/kg+0.15 μg/kg/min), II) PBGACA (30 μg/kg+0.15 μg/kg/min), III) ENOX (0.5 mg/kg+5 μg/kg/min) IV) ENOX (0.5 mg/kg+5 μg/kg/min) plus PBGACA (10 μg/kg+0.15 μg/kg/min), V) heparin (60 U/kg+0.7 U/kg/min), and VI) heparin (60 U/kg+PBGACA (10 μg/kg+0.15 μg/kg/min). All compounds are diluted in saline and bolus injections are made using a volume of 5 mL and constant infusions were made using a volume of 22 mL.

After consistent CFRs are established for at least 20 minutes, compounds are administered as described above and blood flow is monitored during the one hour infusion period. Arterial blood samples are drawn before administration of test agents (control sample) and at 5, 10, 30, and 60 min after administration of compounds. Blood samples are drawn on 1/10 volume of 3.8% trisodium citrate and are used for ex vivo platelet aggregation, platelet count, anti-Xa levels, anti-IIa levels, and coagulation time assays (activated partial thromboplastin time, APTT, and prothrombin time, PT). Blood samples (4.5 mL) obtained for analysis of anti-Xa and anti-IIa levels are collected in chilled syringes containing 0.5 mL trisodium citrate and immediately placed on ice. Mean arterial blood pressure, heart rate and EKG are recorded for the duration of the protocol (Grass polygraph, Model 7D, Grass Instruments, Mass.).

Coagulation times and template bleeding time. Activated partial thromboplastin time (APTT) and prothrombin time (PT) are measured using a Microsample Coagulation Analyzer (MCA210, Bio Data Corp, Horsham, Pa.) and Dade® reagents (Thromboplastin-C Plus and Actin® FS Activated PTT reagent, Baxter Diagnostics, Inc., Deerfield, Ill.).

The APTT is the most widely used method for monitoring intravenous heparin anticoagulation therapy. It is also a fundamental screening test for deficiencies or abnormalities of the intrinsic coagulation factors: VII, IX, XI, XII, and factors common to both the intrinsic and extrinsic pathways: I (fibrinogen), II, V, X. When used in conjunction with deficient substrate plasma, the APTT provides the basis for the quantitation of specific coagulation factors.

The intrinsic capability of blood to form a fibrin clot requires coagulation factors XII, XI, IX, VIII, X, V, II (prothrombin), fibrinogen, platelet lipid, and calcium.

By adding a substance to activate factors XII and XI, the contact factors, the partial thromboplastin time becomes the "activated" partial thromboplastin time (APTT). Because coagulation endpoints are shorter and sharper than with the PTT, the APTT has proven to be a simple and highly reliable measurement of the intrinsic coagulation mechanism.

TEST PROCEDURE

1. Preincubate 0.025M Calcium Chloride to 37° C.
2. Pipette 0.1 mL of reconstituted APTT reagent into a test cuvette.
3. Add 0.1 mL test or control plasma.
4. Incubate at 37° C. for 5 minutes exactly.
5. Add 0.1 mL preincubated Calcium Chloride, simultaneously starting the timer.
6. Record the clotting time.

The prothrombin time is the method for monitoring oral anticoagulation therapy. It is also a fundamental screening test for a deficiency or abnormality of extrinsic coagulation factor VII, and the factors common to both the intrinsic and extrinsic hemostatic pathways: fibrinogen II, V and X. When used in conjunction with deficient substrate plasma, the PT provides the basis for the quantification of specific coagulation factors.

The capability of blood to form a fibrin clot by way of the extrinsic hemostatic pathway requires tissue thromboplastin, calcium, factor VII, factor V, factor X, factor II (prothrombin) and factor I (fibrinogen). When tissue thromboplastin and calcium are added to a sample of citrated plasma, the actions of the intrinsic factors are bypassed and the reaction becomes specific for the coagulation factors involved in the extrinsic and common pathways.

TEST PROCEDURE

1. Preincubate reconstituted PT reagent to 37° C.
2. Pipette 0.1 mL of test or control plasma into a test cuvette.
3. Incubate at 37° C. for at least 2 minutes, but not more than 10 minutes.
4. Inject 0.2 mL of the preincubated reagent, simultaneously starting the timer.
5. Record the clotting time.

Template bleeding time measurements are obtained at the same time points as the blood samples, as mentioned previously. Template bleeding time is measured after a uniform incision is made on the mucous membrane of the inner upper lip with a Surgicutt® automated incision device (ITC, Edison, N.J.). Blood is blotted with Surgicutt® bleeding time blotting paper every 30 seconds, being careful not to disturb the incision site. Template bleeding time is measured from the moment of the incision until the blood no longer stained the blotting paper. Bleeding times of 10 minutes are taken to be maximal.

Anti-Xa and anti-IIa activity

These samples are centrifuged at 1500×g for 10 min at 4° C. The plasma is removed and stored at −70° C. until assayed. Anti-Xa and Anti-IIa activity are analyzed by chromogenic methods using kits supplied by American Diagnostica (actichrome® Heparin and actichrome® Heparin anti-IIa, Greenwich, Conn.), with minor modifications. Incubations and reactions are performed at 37° C. Amidolytic activity (milli-optical units, or mOD) is determined using a SPECTRAmax microtiter plate spectrophotometer and Softmax Pro software (Molecular Devices Corp., Sunnyvale, Calif.). The 1st International LMWH Standard (National Institute for Biological Standards and Control, London; anti-Xa activity 168 IU/ing and anti-IIa activity 66.5 IU/mg) is used to construct standard curves for measuring hieparin and ENOX anti-Xa and anti-IIa activity. The curves are constructed using a four parameter curve-fitting model (Softmax Pro, Molecular Devices, Sunnyvale, Calif.). Values for anti-Xa and anti-IIa activity of heparin and ENOX are reported in International Units.

Platelet aggregation

The Inhibition of ex-vivo Platelet Aggregation assay is based on that of Zucker, "Platelet Aggregation Measured by the Photoelectric Method", Methods in Enzymology 169, 117–133 (1989).

Platelet rich plasma (PRP) is prepared by centrifugation of the blood samples at 150×g for 10 min. After removal of the supernatant containing PRP, platelet-poor plasma (PPP) is prepared by centrifugation of the remaining sample at 1000×g for 10 min. Platelet count is determined with a Coulter ZM or Coulter ZBI particle counter (Coulter Instruments, Hialeah, Fla.). When necessary, platelet count is adjusted to $3 \times 10^8$ platelets/mL using autologous PPP. PRP (250 µL) is incubated at 37° C. while being stirred at 1200 rpm. After preincubation with epinephrine for 1 min (1 µM, Chrono-par 393, Chrono-log Corp., Havertown, Pa.), platelet aggregation is induced by adenosine diphosphate (ADP, 10 µM, Chrono-par 384, Chrono-log Corp., Havertown, Pa.), collagen (equine tendon, 10 µg/mL, Chrono-par 385, Chrono-log Corp., Havertown, Pa.), arachidonic acid (1 mM, Biodata Corp, Horsham, Pa.) or thrombin (4 Units/mL, Enzyme Research Institute, South Bend, Ind.; plus Gly-Pro-Arg-Pro, a fibrin polymerization inhibitor, 2 mM, Sigma Chemical Co., St. Louis, Mo.). Platelet aggregation is monitored spectrophotometrically with a PAP-4C platelet aggregator (Bio Data Corp, Horsham, Pa.). Results are expressed as a percent inhibition of the rate of aggregation as compared to the pre-drug aggregation response.

Statistics

Data obtained by multiple sampling during the experiment are analyzed by two-way repeated measures analysis of variance. Post-hoc multiple comparisons of means to control values within treatment groups, and comparison of ENOX data to other treatment groups, are performed using the least significant difference test. A p-value less than 0.05 is considered significant.

Results

The combined use of an anti-Xa activity compound and a platelet aggregation antagonist compound used according to the invention, provides for use of those compounds at doses that would be subefficacious if used individually, while effecting the inhibition of repetitive platelet thrombus formation to the same extent as high doses of the platelet aggregation antagonist compound without significantly increasing template bleeding time (as compared to: a >5-fold increase in template bleeding time caused by high-dose of the platelet aggregation antagonist compound, BSPBPA; and a ~3-fold increase in template bleeding time caused by high-dose of the platelet aggregation antagonist compound, PBGACA).

Combination of a low-dose of a platelet aggregation antagonist compound with heparin, at a dose which increased APTT 2.0- to 2.5-fold over baseline, did not inhibit repetitive platelet thrombus formation.

The present invention may be embodied in other specific forms without departing from the spirit or essential attributes thereof.

What is claimed is:

1. A pharmaceutical composition comprising a pharmaceutically acceptable carrier and pharmaceutically effective amounts of a compound having anti-Xa activity and a platelet aggregation antagonist compound.

2. The pharmaceutical composition according to claim 1 wherein the compound having anti-Xa activity is a low molecular weight heparin.

3. The pharmaceutical composition according to claim 1 wherein the low molecular weight heparin is selected from the group consisting of enoxaparin, nardroparin, dalteparin, certroparin, parnaparin, reviparin, ardeparin/RD heparin/RDH and tinzaparin.

4. The pharmaceutical composition according to claim 1 wherein the low molecular weight heparin is enoxaparin.

5. The pharmaceutical composition according to claim 1 wherein the compound having anti-Xa activity is a heparinoid compound.

6. The pharmaceutical composition according to claim 1 wherein the heparinoid compound is danaparoid.

7. The pharmaceutical composition according to claim 1 wherein the platelet aggregation antagonist compound is abciximab, N-[N-[N-(4-(piperidin-4-yl)butanoyl)-N-ethylglycyl]aspartyl]-L-β-cyclohexyl alanine, N-[N-[N-(4-(piperidin-4-yl)butanoyl)-N-ethylglycyl]aspartyl]-L-β-cyclohexyl alanine amide or N-(n-butylsulfonyl)-4-(piperidin-4-ylbutyloxy)-L-phenylalanine.

8. The pharmaceutical composition according to claim 7 wherein the platelet aggregation antagonist compound antagonist is abciximab.

9. The pharmaceutical composition according to claim 7 wherein the platelet aggregation antagonist compound is N-[N-[N-(4-(piperidin-4-yl)butanoyl)-N-ethylglycyl] aspartyl]-L-β-cyclohexyl alanine.

10. The pharmaceutical composition according to claim 7 wherein the platelet aggregation antagonist compound is N-[N-[N-(4-(piperidin-4-yl)butanoyl)-N-ethylglycyl] aspartyl]-L-β-cyclohexyl alanine amide.

11. The pharmaceutical composition according to claim 7 wherein the platelet aggregation antagonist compound is N-(n-butylsulfonyl)-4-(piperid in-4-yl butyloxy)-L-phenylalanine.

12. A method of treating or preventing a physiological condition associated with a thrombosis related ischemic disorder in a patient comprising administering to said patient pharmaceutically effective amounts of a compound having anti-Xa activity and a platelet aggregation antagonist compound.

13. The method of claim 12 wherein the physiological condition is selected from the group consisting of stroke, atherosclerosis, angiogenesis, thrombosis, a thromboembolic condition, disseminated intravascular coagulation, peripheral arterial occlusive disease, hemodialysis, an extracorporeal circulation requirement associated with a surgical procedure, tissue damage caused by phospholipases A2, an acute coronary syndrome, and a thromboembolic syndrome associated with cancer, sepsis or obstetrical complications.

14. The method of claim 13 wherein the physiological condition is the acute coronary syndrome.

15. The method of claim 14 wherein the acute coronary syndrome is unstable angina or myocardial infarction.

16. The method of claim 12 wherein the treating or preventing occurs in the course of coronary artery bypass surgery or percutaneous transluminal coronary angioplasty.

17. The method of claim 12 wherein the treating or preventing occurs in the course of percutaneous transluminal coronary angioplasty. carrier.

18. The method of claim 12 wherein the compound having anti-Xa activity is a low molecular weight heparin.

19. The method of claim 18 wherein the low molecular weight heparin is enoxaparin.

20. The method of claim 12 wherein the compound having anti-Xa activity is a heparinoid compound.

21. The method of claim 20 wherein the heparinoid compound is danaparoid.

22. The method of claim 12 wherein the platelet aggregation antagonist compound is selected from the group consisting of abciximab, N-[N-[N-(4-(piperidin-4-yl)butanoyl)-N-ethylglycyl]aspartyl]-L-β-alanine, N-[N-[N-(4-(piperidin-4-yl)butanoyl)-N-ethylglycyl]aspartyl]-L-β-cyclohexyl alanine amide and N-(n-butylsulfonyl)-4-(piperidin-4-ylbutyloxy)-L-phenylalanine.

23. The method of claim 12 wherein the platelet aggregation antagonist compound is abciximab.

24. The method of claim 12 wherein the platelet aggregation antagonist compound is N-(n-butylsulfonyl)-4-(piperidin-4-ylbutyloxy)-L-phenylalanine.

25. A method of effecting the inhibition of repetitive platelet thrombus formation in a patient comprising administering to said patient pharmaceutically effective amounts of a compound having anti-Xa activity and a platelet aggregation antagonist compound; wherein template bleeding time is not significantly increased.

26. The method of claim 25 wherein template bleeding time is increased less than three-fold.

27. The method of claim 25 wherein the inhibition of repetitive platelet thrombus formation is greater than the inhibition resulting from administration of the same dosage of platelet aggregation antagonist compound without coadministration of a compound having anti-Xa activity.

28. The method of claim 27 wherein the compound having anti-Xa activity is a low molecular weight heparin.

29. The method of claim 28 wherein the platelet aggregation antagonist compound is selected from the group consisting of abciximab, N-[N-[N-(4-(piperidin-4-yl)butanoyl)-N-ethylglycyl]aspartyl]-L-β-cyclohexyl alanine, N-[N-[N-(4-(piperidin-4-yl)butanoyl)-N-ethylglycyl]aspartyl]-L-β-cyclohexyl alanine amide and N-(n-butylsulfonyl)-4-(piperidin-4-ylbutyloxy)-L-phenylalanine.

30. A method of treating or preventing a physiological condition associated with a thrombosis related ischemic disorder in a patient comprising administering to said patient pharmaceutically effective amounts of a compound having anti-Xa activity and a platelet aggregation antagonist compound; wherein repetitive platelet thrombus formation is inhibited without significantly increasing template bleeding time.

31. The method of claim 30, wherein the compound having anti-Xa activity is a low molecular weight heparin and the platelet aggregation antagonist compound is abciximab or N-(n-butylsulfonyl)-4-(piperidin-4-ylbutyloxy)-L-phenylalanine.

32. A method of combination therapy for treating or preventing a physiological condition associated with a thrombosis related ischemic disorder in a patient comprising administering to said patient pharmaceutically effective amounts of a compound having anti-Xa activity and a platelet aggregation antagonist compound; wherein inhibition of repetitive platelet thrombus formation is greater with the combination therapy than inhibition resulting from administration of platelet aggregation antagonist compound without coadministration of the compound having anti-Xa activity.

33. The method of claim 32 wherein the compound having anti-Xa activity is a low molecular weight heparin.

34. The method of claim 33 wherein the low molecular weight heparin is enoxaparin.

35. The method of claim 34 wherein the platelet aggregation antagonist compound is abciximab or N-(n-butylsulfonyl)-4-(piperidin-4-ylbutyloxy)-L-phenylalanine.

36. The method of claim 32 wherein the platelet aggregation antagonist compound is abciximab or N-(n-butylsulfonyl)-4-(piperidin-4-ylbutyloxy)-L-phenylalanine.

* * * * *